United States Patent
Kamei et al.

(10) Patent No.: US 7,105,359 B2
(45) Date of Patent: Sep. 12, 2006

(54) SPECIFIC COUPLING REACTION MEASURING METHOD AND REAGENT KIT AND SPECIFIC COUPLING REACTION MEASURING APPARATUS FOR USE IN THE SAME

(75) Inventors: Akihito Kamei, Kyoto (JP); Nobuyuki Shigetoh, Kyoto (JP); Tatsurou Kawamura, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/704,802

(22) Filed: Nov. 12, 2003

(65) Prior Publication Data

US 2004/0096909 A1    May 20, 2004

(30) Foreign Application Priority Data

Nov. 12, 2002  (JP)  .............................. 2002-328056

(51) Int. Cl.
*G01N 33/553*    (2006.01)

(52) U.S. Cl. .................... 436/526; 436/518; 436/524; 436/525; 436/164; 435/7.1; 435/287.2

(58) Field of Classification Search .................... 435/4, 435/6, 7.1, 7.2, 7.9, 7.92, 283.1, 287.2, 287.1; 436/526, 525, 524, 164, 518
See application file for complete search history.

(56) References Cited

U.S. PATENT DOCUMENTS

| | | | | |
|---|---|---|---|---|
| 4,115,534 A | * | 9/1978 | Ithakissios | 435/500 |
| 4,141,687 A | * | 2/1979 | Forrest et al. | 436/526 |
| 5,145,784 A | * | 9/1992 | Cox et al. | 436/526 |
| 5,238,810 A | | 8/1993 | Fujiwara et al. | |
| 5,369,037 A | * | 11/1994 | Hansen | 436/533 |
| 5,470,534 A | * | 11/1995 | Imai et al. | 422/67 |
| 5,508,164 A | * | 4/1996 | Kausch et al. | 435/6 |
| 5,993,740 A | | 11/1999 | Niiyama et al. | |
| 6,087,182 A | * | 7/2000 | Jeng et al. | 436/66 |
| 6,254,830 B1 | * | 7/2001 | Pivarnik et al. | 422/82.07 |
| 6,264,825 B1 | * | 7/2001 | Blackburn et al. | 205/777.5 |
| 6,432,290 B1 | * | 8/2002 | Harrison et al. | 204/453 |
| 6,432,630 B1 | * | 8/2002 | Blankenstein | 435/4 |

(Continued)

FOREIGN PATENT DOCUMENTS

EP    0 262 760 A1    4/1988

(Continued)

OTHER PUBLICATIONS

Nakamura et al., Detection and Removal of *Escherichia coli* Using Fluorescein Isothiocyanate Conjugated Monoclonal Antibody Immobilized on Bacterial Magnetic Particles, Aug. 1, 1993;Analytical Chemistry, vol. 65, No. 15, pp. 2036-2039.*

(Continued)

*Primary Examiner*—Long V. Le
*Assistant Examiner*—Melanie Yu
(74) *Attorney, Agent, or Firm*—McDermott Will & Emery LLP

(57) ABSTRACT

A specific coupling reaction measuring method of this invention for measuring a content of a subject substance in a sample includes the steps of (a) constructing a reaction system including the sample and a magnetic particle on which a specific coupling substance for specifically coupling with the subject substance is immobilized; (b) measuring an optical characteristic of the reaction system; and (c) removing, from the reaction system, an agglutination complex including the subject substance, the specific coupling substance and the magnetic particle by utilizing magnetic force.

8 Claims, 12 Drawing Sheets

U.S. PATENT DOCUMENTS

| | | | |
|---|---|---|---|
| 6,440,725 B1* | 8/2002 | Pourahmadi et al. | 435/288.5 |
| 6,514,770 B1* | 2/2003 | Sorin | 436/518 |
| 6,586,193 B1* | 7/2003 | Yguerabide et al. | 435/7.92 |
| 6,632,655 B1* | 10/2003 | Mehta et al. | 435/288.5 |
| 6,649,419 B1* | 11/2003 | Anderson | 436/526 |
| 6,878,558 B1* | 4/2005 | Uchida et al. | 436/518 |
| 2001/0054580 A1* | 12/2001 | Watkins et al. | 210/222 |
| 2004/0219695 A1* | 11/2004 | Fox | 436/526 |

FOREIGN PATENT DOCUMENTS

| | | |
|---|---|---|
| JP | 5-2024 A | 1/1993 |
| JP | 2927082 | 5/1999 |
| JP | 2000-346843 A | 12/2000 |
| WO | WO 99/27369 A | 6/1999 |
| WO | WO 01/14591 A1 | 3/2001 |

OTHER PUBLICATIONS

Izumi, Kanai, ediited by Masamitsu Kanai, Summary of clinical examinations:, revised edition 31, published by Kanahara Shuppan Kabushiki Kaisha, 1998, p. 156 and pp. 179-180.

Shuppan, Kanahara, "Summary of Clinical Examination." 31st Edition, pp. 1-3 of Partial English Translation, pp. 1-5 pages total of Japanese Publication.

Lim, Pak-Leong et al., "One-Step 2 Minute Test To Detect Typhoid-Specific Antibodies Based on Particle Separation in Tubes." Journal of Clinical Microbiology, Aug. 1998, pp. 2271-2278, XP-001179896.

* cited by examiner

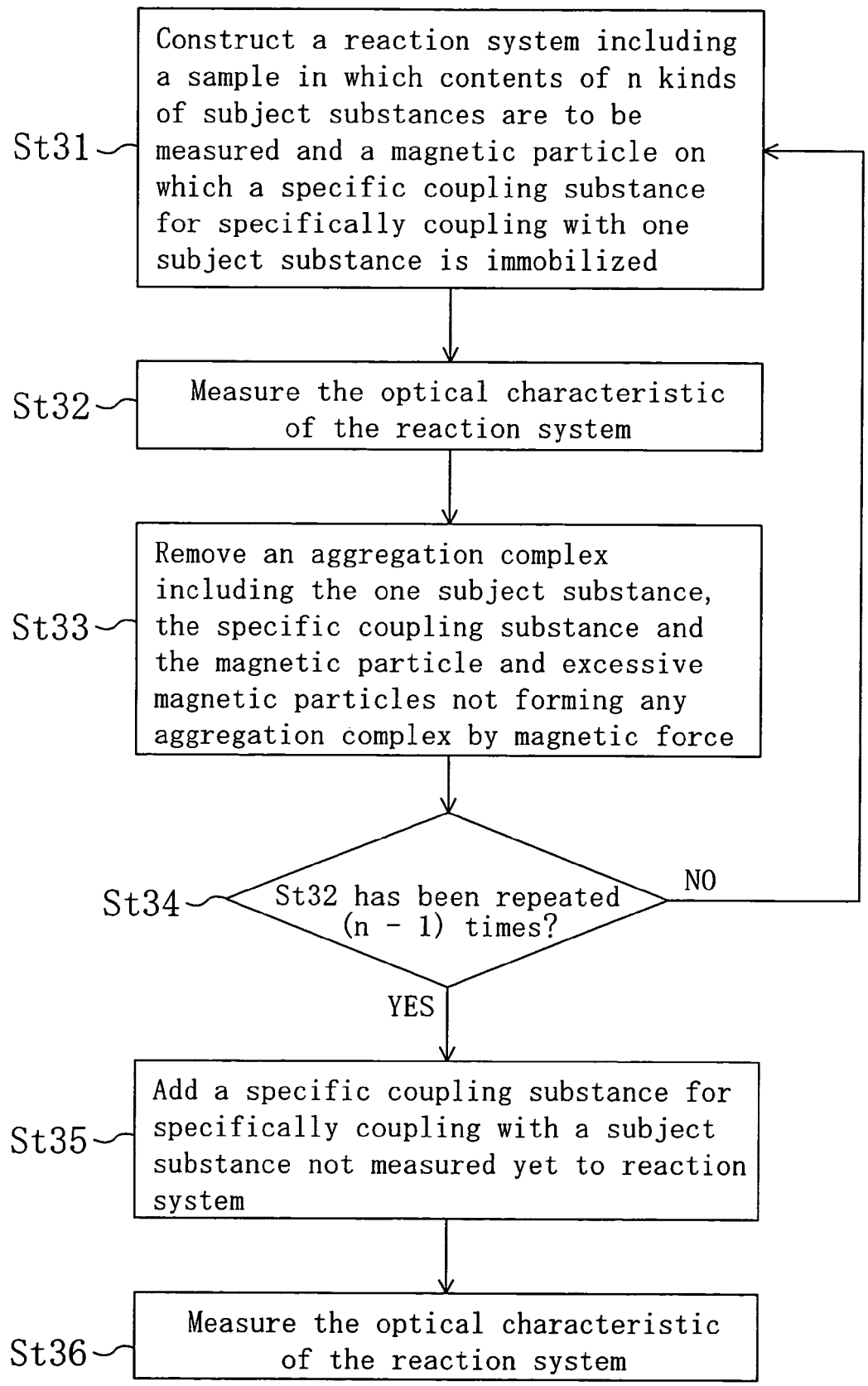

SPECIFIC COUPLING REACTION MEASURING METHOD AND REAGENT KIT AND SPECIFIC COUPLING REACTION MEASURING APPARATUS FOR USE IN THE SAME

BACKGROUND OF THE INVENTION

The present invention relates to a specific coupling reaction measuring method for measuring the content of a substance to be measured (hereinafter referred to as a subject substance) that may be included in a sample, and a reagent kit and a specific coupling reaction measuring apparatus for use in the specific coupling reaction measuring method.

In the field of medical care, the content of a protein peculiar to each disease present in a human body fluid is generally measured for diagnosis of various diseases or for examination of the progressing condition of a disease. In the measurement of the content of a protein, a specific coupling reaction measuring method utilizing a reaction between an antigen and an antibody for specifically recognizing a target protein as an antigen (namely, an antigen-antibody reaction) is widely used. Currently, a variety of specific coupling reaction measuring methods respectively based on various principles have been developed.

Among these various specific coupling reaction measuring methods, well-known measuring methods are immune nephelometry (hereinafter referred to simply as the nephelometry), immune turbidimetry (hereinafter referred to simply as the turbidimetry) and a slide agglutination in all of which agglutination of an antigen-antibody complex generated through an antigen-antibody reaction (hereinafter referred to as the agglutination complex) is detected in order to measure the content of a subject substance in a sample. In the antigen-antibody reaction, turbidity is caused in the reaction system due to the generation of the agglutination complex. The extent of the turbidity caused in the reaction system due to the generation of the agglutination complex depends upon the quantity of the antigen and the quantity of the antibody. On the basis of this, the extent of the turbidity caused in the reaction system is optically measured in the nephelometry and the turbidimetry, so as to calculate the quantity of the antigen or the antibody based on the optically measured value. Specifically, the agglutination complex is measured on the basis of change in the quantity of light scattered in the reaction system according to the nephelometry and is measured on the basis of change in the quantity of transmitted light reduced through the scattering in the reaction system according to the turbidimetry. In general, the same reaction system can be used in the measurement by these two methods. In other words, a reaction system that can be dealt with by one of these methods can be dealt with by the other method. In the slide agglutination, turbidity or aggregate caused in a reaction system due to generation of an agglutination complex is visually measured on a slide glass or the like. Also in the slide agglutination, the same reaction system as that usable in the nephelometry and the turbidimetry can be used. In these three measuring methods, the measurement is performed by using a reaction system in which an antigen and an antibody are homogeneously dispersed, and hence these methods are known generically as an "specific coupling reaction measuring method for a homogeneous system".

Also, in the field of the medical care, the contents of several kinds of subject substances are measured for diagnosis of various diseases or for examination of the progressing condition of a disease. For example, in a clinical examination, the contents of all proteins in a humane urine are measured as an index of the filtering function of a kidney, or the content of erythrocyte (hemoglobin) in a humane urine is measured as an index of inflammation, calculosis or a tumor of a urinary tract such as acute glomerulonephritis, IgA nephropathy, nephrophthisis, renal infarction, interstitial nephritis, cystitis, urethritis or prostatitis (for example, see Non-Patent Document 1 below). Furthermore, Patent Document 2 below discloses, as a specific coupling reaction measuring method for a homogeneous system for measuring several kinds of subject substances, a method in which different reaction vessels are prepared for respective subject substances for individually measuring the subject substances.

It should be noted that methods of measuring the content of a subject substance in a sample by using a reaction of the subject substance included in the sample to a specific coupling substance for specifically coupling with the subject substance is referred to as "specific coupling reaction measuring method" in the present description. The aforementioned immune reaction measuring methods are also examples of the specific coupling reaction measuring methods.

Patent Document 1: Japanese Laid-Open Patent Publication No. 5-2024

Non-Patent Document 1: "Summary of clinical examinations", written by Izumi Kanai, edited by Masamitsu Kanai, revised edition 31, published by Kanahara Shuppan Kabushiki Kaisha, 1998, p. 156 and pp. 179–180

However, in any of the aforementioned conventional methods, for measuring a plurality of kinds of subject substances, it is necessary to prepare reaction vessels in the same number as the number of kinds of subject substances, and hence a large quantity of sample is necessary.

SUMMARY OF THE INVENTION

The present invention was devised in consideration of the aforementioned conventional situations, and an object of the invention is providing a specific coupling reaction measuring method in which a plurality of subject substances can be measured within one reaction vessel, and a reagent kit and a specific coupling reaction measuring apparatus for use in the specific coupling reaction measuring method.

The specific coupling reaction measuring method of this invention for measuring a content of a subject substance in a sample, includes the steps of (a) constructing a reaction system including the sample and a magnetic particle on which a specific coupling substance for specifically coupling with the subject substance is immobilized; (b) measuring an optical characteristic of the reaction system; and (c) removing, from the reaction system, an agglutination complex including the subject substance, the specific coupling substance and the magnetic particle by utilizing magnetic force.

In this method, excessive magnetic particle present in the reaction system and the agglutination complex including the subject substance, the specific coupling substance and the magnetic particle are removed from the reaction system by utilizing the magnetic force in the step (c) after the measurement. Particularly, since the magnetic force is used in this invention, the reaction system is not chemically affected at all. Therefore, the reaction system obtained after the measurement can be used for measuring another component of the sample by any of various measuring methods.

Also, in the conventional technique to measure two kinds of subject substances, it is necessary to prepare reaction vessels in the same number as the number of kinds of subject substances. In contrast, according to this invention, merely one reaction vessel in which a reaction system can be constructed can be used for measuring two kinds of subject substances. Accordingly, the quantity of a sample necessary for the measurement can be very small in this embodiment. As a result, in the field of, for example, medical care, the quantity of a sample to be drawn from a patient can be reduced, so as to lighten a burden of the patient.

In one aspect, the optical characteristic may be the intensity of scattered light or the quantity of transmitted light.

In one aspect, the magnetic particle preferably has a diameter of approximately 0.05 through 2 µm.

In another aspect, the magnetic particle remaining in the reaction system is removed from the reaction system in the step (c).

Another specific coupling reaction measuring method of this invention for measuring contents of a first subject substance and a second subject substance in a sample, includes the steps of (a) constructing a reaction system including the sample and a magnetic particle on which a first specific coupling substance for specifically coupling with the first subject substance is immobilized; (b) measuring an optical characteristic of the reaction system after the step (a); (c) collecting an agglutination complex including the first subject substance, the first specific coupling substance and the magnetic particle by utilizing magnetic force; (d) adding, to the reaction system, a second specific coupling substance for specifically coupling with the second subject substance; and (e) measuring an optical characteristic of the reaction system after the step (d).

In this method, in measuring the second subject substance, change in the optical characteristic of the reaction system caused by the agglutination complex including the subject substance, the specific coupling substance and the magnetic particle is removed by utilizing the magnetic force. Particularly, since the magnetic force is used, the reaction system is not chemically affected at all. Therefore, this specific coupling reaction measuring method can attain high reliability also in a measured value of the second subject substance.

Also, in the conventional technique to measure two kinds of subject substances, it is necessary to prepare reaction vessels in the same number as the number of kinds of subject substances. In contrast, according to this invention, merely one reaction vessel in which a reaction system can be constructed can be used for measuring two or more kinds of subject substances. Accordingly, the quantity of a sample necessary for the measurement can be very small in this embodiment. As a result, in the field of, for example, medical care, the quantity of a sample to be drawn from a patient can be reduced, so as to lighten a burden of the patient.

In one aspect, the reaction system preferably includes 2 through 6 wt % of polyethylene glycol in the step (d).

In one aspect, the second specific coupling substance is preferably composed of an antigen or antibody for specifically coupling with the second subject substance and a nonmagnetic particle on which the antigen or antibody is immobilized.

In one aspect, the magnetic particle preferably has a diameter of approximately 0.05 through 2 µm and the nonmagnetic particle preferably has a diameter of approximately 0.05 through 2 µm.

In one aspect, a combination of the first subject substance and the second subject substance may be a combination of human hemoglobin and human albumin.

In another aspect, the magnetic particle remaining in the reaction system is collected in the step (c).

Still another specific coupling reaction measuring method of this invention for measuring contents of n kinds (wherein n is an integer of 2 or more) of subject substances in a sample, includes the steps of (a) constructing a reaction system including the sample and a magnetic particle on which a specific coupling substance for specifically coupling with one subject substance out of subject substances not measured yet is immobilized; (b) measuring an optical characteristic of the reaction system after the step (a); (c) removing, from the reaction system, an agglutination complex including the one subject substance, the specific coupling substance and the magnetic particle by utilizing magnetic force; (d) determining to return to the step (a) when the step (b) has not been repeated (n−1) times; (e) adding, to the reaction system, a specific coupling substance for specifically coupling with one remaining subject substance not measured yet in the reaction system; and (f) measuring an optical characteristic of the reaction system after the step (e).

In this method, the agglutination complex including the subject substance, the specific coupling substance and the magnetic particle is removed by utilizing the magnetic force after measuring the optical characteristic. Since the magnetic force is used, the reaction system is not chemically affected at all. Therefore, even when a plurality of subject substances are measured, the influence of a previously formed agglutination complex is substantially eliminated, so that every measurement can attain high reliability in a measured value of the optical characteristic.

In particular, in the conventional technique to measure two or more kinds of subject substances, it is necessary to prepare reaction vessels in the same number as the number of kinds of subject substances. In contrast, according to this embodiment, merely one reaction vessel in which a reaction system can be constructed can be used for measuring two or more kinds of subject substances. Accordingly, the quantity of a sample necessary for the measurement can be very small in this embodiment. As a result, in the field of, for example, medical care, the quantity of a sample to be drawn from a patient can be reduced, so as to lighten a burden of the patient.

In one aspect, the magnetic particle remaining the reaction system is removed from the reaction system in the step (c).

Still another specific coupling reaction measuring method of this invention for measuring contents of n kinds (wherein n is an integer of 2 or more) of subject substances in a sample, includes the steps of (a) constructing a reaction system including the sample and a specific coupling substance for specifically coupling with one subject substance out of subject substances not measured yet; (b) measuring an optical characteristic of the reaction system after the step (a); (c) adding, to the reaction system, a magnetic complex including a magnetic particle and a substance capable of coupling with an agglutination complex including the one subject substance and the specific coupling substance; (d) removing, by utilizing magnetic force, the agglutination complex coupled with the magnetic complex; (e) determining, after the step (d), to return to the step (a) when the step (b) has not been repeated (n−1) times; (f) adding, to the reaction system, a specific coupling substance for specifically coupling with one remaining subject substance not measured yet in the reaction system; and (g) measuring an optical characteristic of the reaction system after the step (f).

In this method, the agglutination complex including the subject substance and the specific coupling substance is removed by utilizing the magnetic force after measuring the optical characteristic. Since the magnetic force is used, the reaction system is not chemically affected at all. Therefore, even when a plurality of subject substances are measured, the influence of a previously formed agglutination complex is substantially eliminated, so that every measurement can attain high reliability in a measured value of the optical characteristic.

In particular, in the conventional technique to measure two or more kinds of subject substances, it is necessary to prepare reaction vessels in the same number as the number of kinds of subject substances. In contrast, according to this embodiment, merely one reaction vessel in which a reaction system can be constructed can be used for measuring two or more kinds of subject substances. Accordingly, the quantity of a sample necessary for the measurement can be very small in this embodiment. As a result, in the field of, for example, medical care, the quantity of a sample to be drawn from a patient can be reduced, so as to lighten a burden of the patient.

In one aspect, the magnetic complex not coupled with the agglutination complex is removed from the reaction system in the step (d).

The reagent kit of this invention for measuring contents of a first subject substance and a second subject substance in a sample, includes a magnetic particle on which a first specific coupling substance for specifically coupling with the first subject substance is immobilized; and a second specific coupling substance for specifically coupling with the second subject substance.

When this reagent kit of the invention is used in a specific coupling reaction measuring method, the contents of two or more kinds of subject substances can be measured with merely one reaction vessel in which a reaction system can be constructed. Accordingly, the quantity of a sample necessary for the measurement can be very small.

In one aspect, the magnetic particle preferably has a diameter of approximately 0.05 through 2 μm.

In one aspect, the second specific coupling substance is preferably composed of an antigen or antibody for specifically coupling with the second subject substance and a nonmagnetic particle on which the antigen or antibody is immobilized.

Another reagent kit of this invention for measuring contents of n kinds (wherein n is an integer of 2 or more) of subject substances in a sample, includes one specific coupling substance for specifically coupling with one subject substance out of the n kinds of subject substances; and (n−1) kinds of magnetic particles on which specific coupling substances for respectively specifically coupling with the other (n−1) kinds of subject substances out of the n kinds of subject substances are respectively immobilized.

When this reagent kit of the invention is used in a specific coupling reaction measuring method, the contents of two or more kinds of subject substances can be measured with merely one reaction vessel in which a reaction system can be constructed. Accordingly, the quantity of a sample necessary for the measurement can be very small.

Still another reagent kit of this invention for measuring contents of n kinds (wherein n is an integer of 2 or more) of subject substances in a sample, includes n kinds of specific coupling substances for respectively specifically coupling with the n kinds of subject substances; and magnetic complexes each including a substance capable of coupling with an agglutination complex including a combination of each of (n−1) kinds of subject substances out of the n kinds of subject substances and each of (n−1) kinds of corresponding specific coupling substances, and a magnetic particle on which the substance is immobilized.

When this reagent kit of the invention is used in a specific coupling reaction measuring method, the contents of two or more kinds of subject substances can be measured with merely one reaction vessel in which a reaction system can be constructed. Accordingly, the quantity of a sample necessary for the measurement can be very small.

The specific coupling reaction measuring apparatus of this invention includes a cell; a light source for emitting light to the cell; a photodetector for detecting scattered light or transmitted light received from a reaction system constructed in the cell; and removing means for removing a magnetic particle from the cell by utilizing magnetic force when the cell contains the magnetic particle.

This specific coupling reaction measuring apparatus is suitably used for any of the above-described specific coupling reaction measuring methods of this invention.

BRIEF DESCRIPTION OF THE DRAWINGS

FIG. 5 is a flowchart of a specific coupling reaction measuring method according to still another embodiment of the invention;

DETAILED DESCRIPTION OF THE INVENTION

Figure 1:
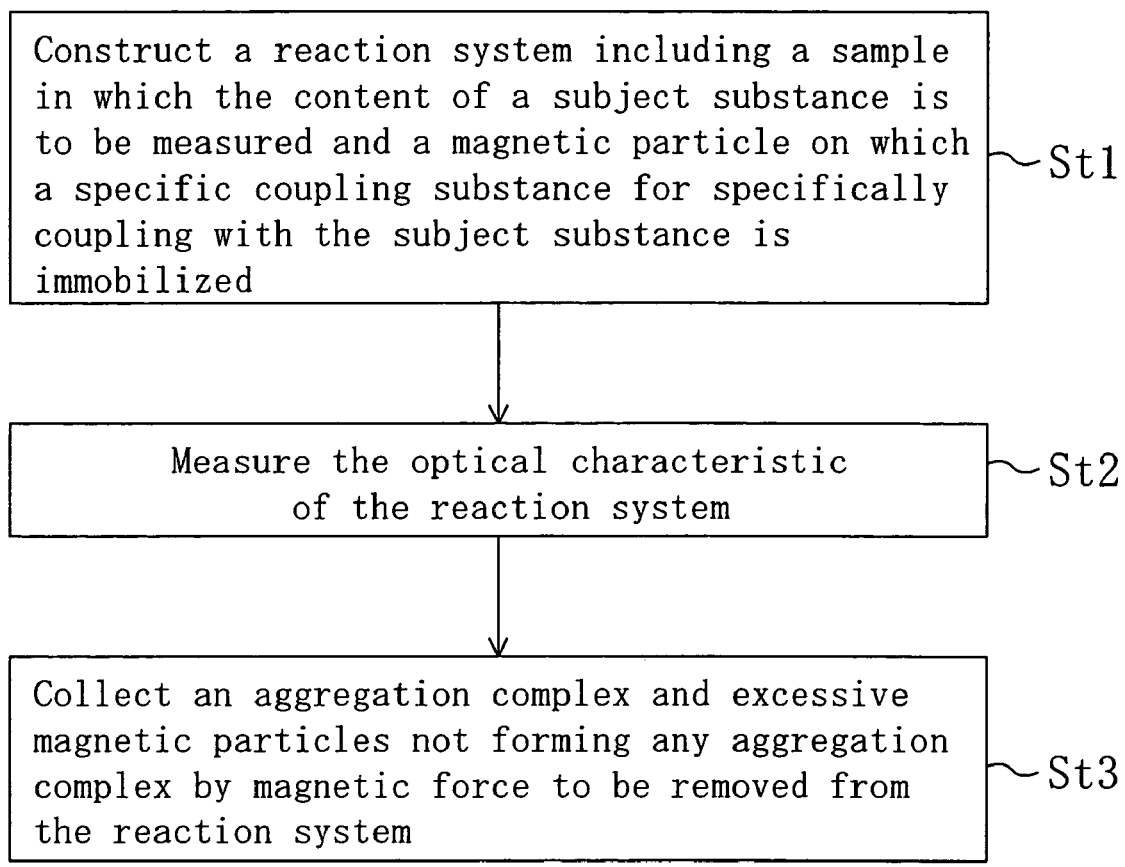
FIG. 1 is a flowchart of a specific coupling reaction measuring method according to an embodiment of the invention.

Immune reaction measuring methods, which are example of specific coupling reaction measuring methods, will now be described in the following embodiments with reference to the accompanying drawings. For simplification, like reference numerals are used to refer to like elements commonly used in the respective embodiments.

EMBODIMENT 1

Figure 2A:
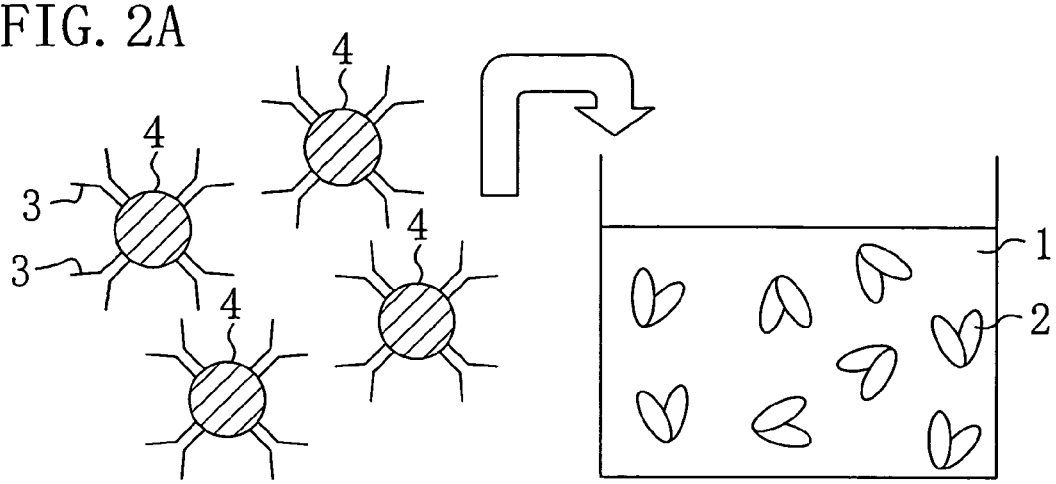
FIGS. 2A, 2B and 2C are schematic diagrams of a reaction system in respective procedures in the specific coupling reaction measuring method of FIG. 1.
Figure 2B:
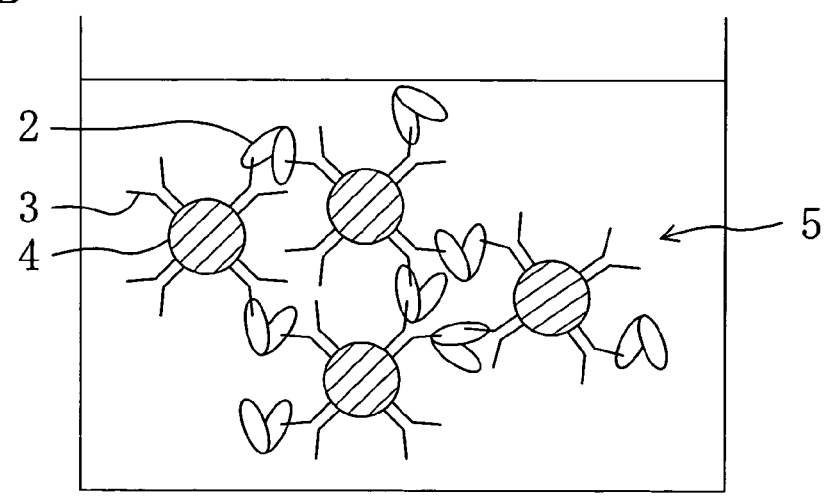
Figure 2C:
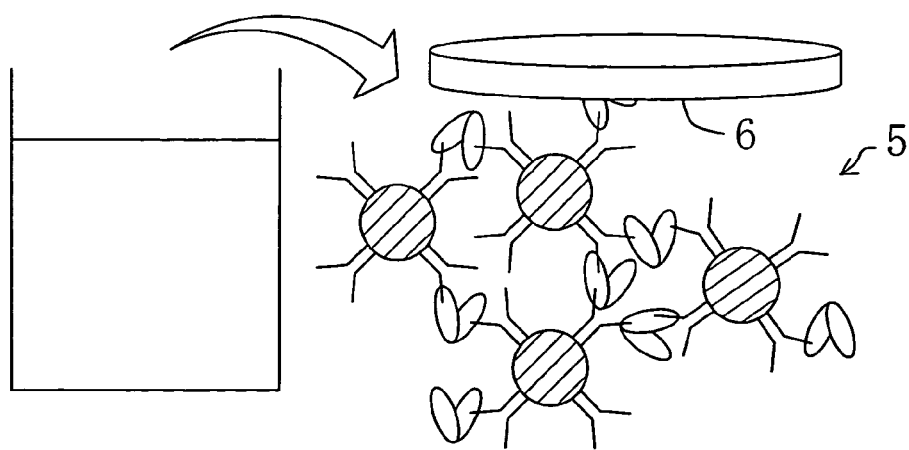

FIG. 1 is a flowchart of a specific coupling reaction measuring method of this embodiment. FIGS. 2A through 2C are schematic diagrams of a reaction system in respective procedures in the specific coupling reaction measuring method of this embodiment.

First, in step St1 of FIG. 1, a reaction system including a sample 1 in which the content of a subject substance 2 is to be measured and a magnetic particle 4 on which a specific coupling substance 3 for specifically coupling with the subject substance 2 is immobilized is constructed as shown in FIG. 2A. The sample 1 can be, for example, a body fluid such as a blood or a urine itself, or a mixture of such a body fluid and a buffer. In the case where the subject substance 2 is an antigen, the specific coupling substance 3 is an antibody, and in the case where the subject substance 2 is an antibody, the specific coupling substance 3 is an antigen.

In this manner, when the subject substance 2 is included in the sample, an agglutination complex 5 including the subject substance 2, the specific coupling substance 3 and the magnetic particle 4 is generated through an antigen-antibody reaction between the subject substance 2 and the specific coupling substance 3 as shown in FIG. 2B. When the subject substance 2 is not included in the sample, the agglutination complex 5 resulting from the antigen-antibody reaction between the subject substance 2 and the specific coupling substance 3 is not generated.

Next, in step St2 of FIG. 1, an optical characteristic of the reaction system is measured. At this point, in the case where the agglutination complex 5 has been generated in step St1, turbidity is caused in the reaction system, and hence, the intensity of scattered light and the quantity of transmitted light are changed. Accordingly, the extent of the turbidity of the reaction system can be estimated by measuring the intensity of scattered light or the quantity of transmitted light. At this point, the optical change of the reaction system, namely, the change in the intensity of scattered light or the quantity of transmitted light, is preferably measured with reference to that of the sample 1 obtained before the measurement. When the reaction system is constructed by using the mixture with a buffer as the sample 1, the buffer may be used as a reference.

Next, in step St3 of FIG. 1, the agglutination complex 5 including the subject substance 2, the specific coupling substance 3 and the magnetic particle 4 and excessive magnetic particles not forming any agglutination complex 5 (not shown) are collected by utilizing magnetic force (that is, specifically, a magnet 6 as shown in FIG. 2C) to be removed from the reaction system.

In the specific coupling reaction measuring method, the extent of the turbidity resulting from the generation of the agglutination complex depends upon the quantity of an antigen and the quantity of an antibody. Accordingly, in this embodiment, the optical characteristic of the reaction system is measured, and the content of the subject substance 2 can be calculated on the basis of the measured value of the optical characteristic.

Furthermore, in this embodiment, the excessive magnetic particles present in the reaction system and the agglutination complex 5 including the subject substance 2, the specific coupling substance 3 and the magnetic particle 4 are removed from the reaction system by utilizing the magnetic force after the measurement. Since the magnetic force is used in this embodiment, the reaction system is not chemically affected at all. Therefore, the reaction system obtained after the measurement can be used for measuring another component of the sample 1 by any of various measuring methods.

Also, in the conventional technique to measure two or more kinds of subject substances, it is necessary to prepare reaction vessels in the same number as the number of kinds of subject substances. In contrast, according to this embodiment, merely one reaction vessel in which a reaction system can be constructed can be used for measuring two or more kinds of subject substances. Accordingly, the quantity of a sample necessary for the measurement can be very small in this embodiment. As a result, in the field of, for example, medical care, the quantity of a sample to be drawn from a patient can be reduced, so as to lighten a burden of the patient.

Moreover, the magnetic particle can be collected to be recycled, with the immobilized antibody or antigen having reactivity, from the agglutination complex 5 and the excessive magnetic particles (not shown) removed from the reaction system in this embodiment by inhibiting the antigen-antibody reaction under an acidic condition of pH 3.0 or less. Alternatively, the antigen or antibody immobilized on the magnetic particle can be completely removed through a treatment with a strong acid or alkali and washing with a surfactant, so that the resultant magnetic particle can be used for immobilizing another antibody or antigen.

The magnetic particles 4 used in the specific coupling reaction measuring method of this embodiment are preferably insoluble in the reaction system. Specific examples of the magnetic particles 4 are ferrite particles, ferrite colloid particles and ferrite-containing latex particles. Such magnetic particles can be prepared by a user. In particular, magnetic particles having substantially uniform diameters can be obtained as follows: Magnetic bacteria somatically including magnetic particles of 0.05 through 0.1 µm are cultured to increase the number of bacteria; the resultant bacteria are spalled with a French press or the like; and the magnetic particles of the bacteria are collected by using a magnet to be separately taken out. The method for obtaining the magnetic particles from the magnetic bacteria is more specifically described in Japanese Laid-Open Patent Publication No. 2000-346843.

The magnetic particle obtained from the magnetic bacterium is covered with a lipid bilayer. Therefore, such magnetic particles are well dispersed in an aqueous solution or the like and are suitably used for immobilizing a protein such as an antibody used as the specific coupling substance.

The diameter of the magnetic particle 4 used in this embodiment is preferably 0.05 through 2 µm because magnetic particles with such a diameter can be easily homogeneously dispersed in an aqueous solution and can allow the change in the intensity of scattered light or the quantity of transmitted light to be detected for determining the agglutination complex generated through the antigen-antibody reaction.

The magnet 6 is used for generating the magnetic force to collect the magnetic particles in this embodiment, and the magnet 6 is more specifically a permanent magnet or an electromagnet.

The reaction system used in the specific coupling reaction measuring method of this embodiment may additionally include an arbitrary known component in accordance with the application. For example, in order to reduce nonspecific agglutination through autoagglutinin of the subject substance 2 and the specific coupling substance 3, a surfactant such as Tween 20, octyl glucoside, sodium lauryl sulfate (SDS), sucrose monolaurate or CHAPS may be added to the reaction system of this embodiment. The content of the surfactant in the reaction system is preferably 0.3 wt % or less and more preferably 0.1 wt % or less because the surfactant of such a content minimally affects the antigen-antibody reaction.

In the specific coupling reaction measuring method of this embodiment, as the optical characteristic measured in step St2, change in the intensity of scattered light may be measured (as in the nephelometry) or change in the quantity of transmitted light may be measured (as in the turbidimetry).

The subject substance of this embodiment is not particularly specified but may be any substance that can be measured by utilizing an antigen-antibody reaction. Examples of the subject substance are protein, nucleic acid, lipid, bacteria, virus and hapten. In particular, the specific coupling reaction measuring method of this embodiment is suitably used for measuring a protein that is conventionally measured by utilizing an antigen-antibody reaction in the clinical examination. Examples of the protein are hormones such as LH (luteinzing hormone), FSH (follicle-stimulating hormone) and hCG (human chorionic gonadotropin), various immunoglobulin classes and sub-classes, a component of complement, markers of various infectious diseases, CRP, albumin, hemoglobin, rheumatoid factors and blood group antigens.

The antibody used in this embodiment is not particularly specified as far as it can produce an agglutination complex together with an antigen by specifically coupling with the antigen. Examples of the antibody are antibodies of any antibody class of IgG, IgM, IgE, IgA or IgD, and a mixture of any of these antibodies. Also, the antibody may be a polyclonal antibody or a monoclonal antibody, or a mixture of them. Among these antibodies, IgG antibodies are preferred because they are less nonspecifically reacted and are comparatively easily commercially available and hence are easily obtained. Also, the kind of original animal of the antibody is not particularly specified, and antibodies derived from a rabbit, a goat and a mouse are preferred because they are comparatively easily obtained and widely used.

Although an immune reaction measuring method utilizing an antigen-antibody reaction is described as a specific coupling reaction measuring method in this embodiment, the measurement can be performed by generating an agglutination complex by using another reaction for causing specific coupling other than the antigen-antibody reaction. When another reaction for causing specific coupling other than the antigen-antibody reaction is used, a combination of a subject substance and a specific coupling substance can be, for example, a combination of a ligand and a receptor or a combination of a single-stranded DNA (subject substance) and various DNA fragments (specific coupling substance) having complementary sequences of the single-stranded DNA.

An example of the combination of a ligand and a receptor is a combination of a molecule working as a ligand and an allosteric protein having a plurality of coupling sites with the molecule. In the case where the molecule working as a ligand has merely one site to be coupled with an allosteric protein, an agglutination complex including the molecule working as a ligand and the allosteric protein can be generated by immobilizing the molecule working as a ligand on a magnetic particle with a site other than that to be coupled with the allosteric protein.

Alternatively, in the case of a single-stranded DNA (subject substance) and various DNA fragments (specific coupling substance) having complementary sequences of the single-stranded DNA, so as to form agglutination complex, the various DNA fragments may be immobilized on a magnetic particle so as to be complementarily capable of coupling with the single-stranded DNA.

EMBODIMENT 2

In Embodiment 2 of the invention, a specific coupling reaction measuring method in which contents of two kinds of subject substances can be measured will be described with reference to the accompanying drawings.

Figure 3:
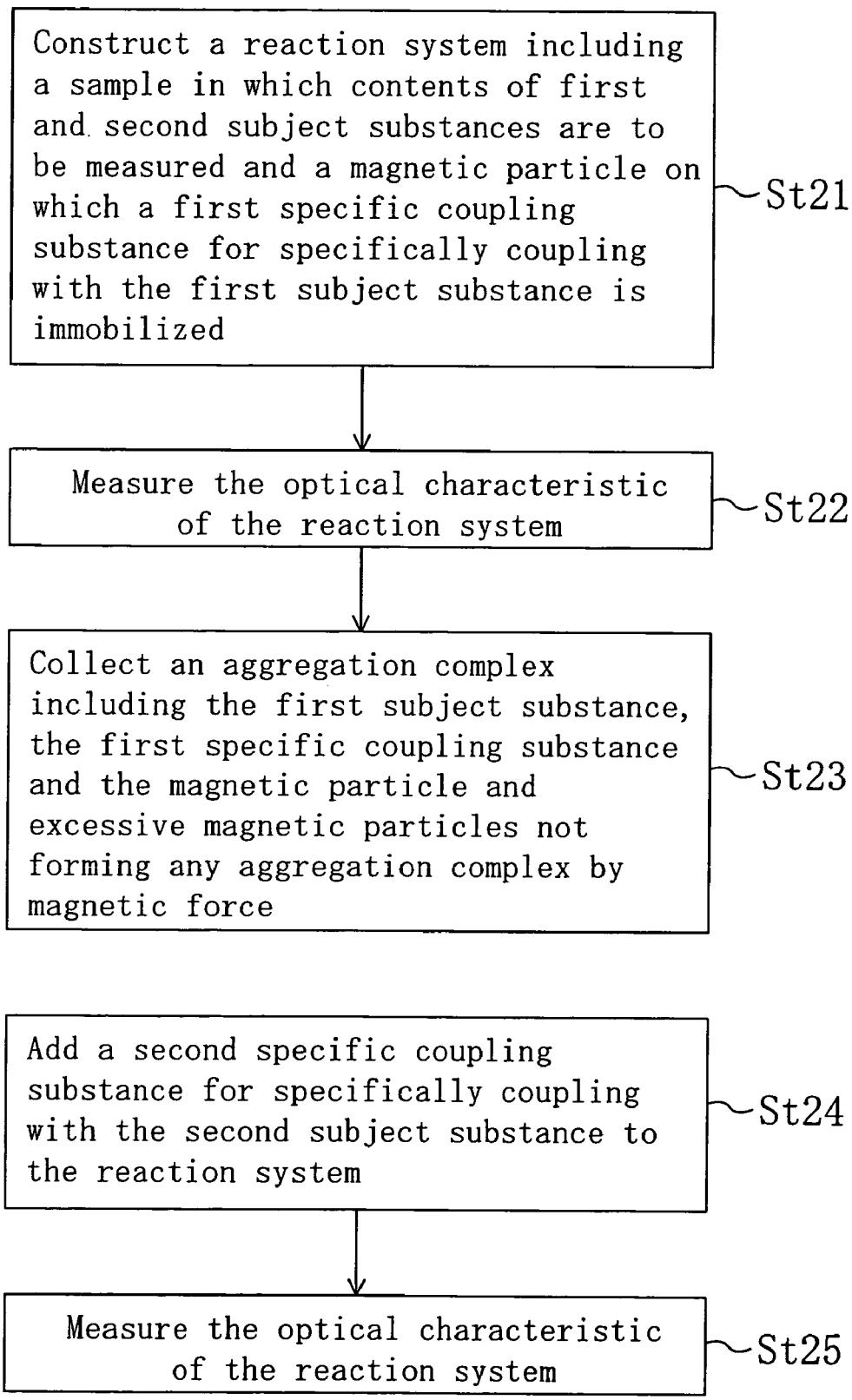
FIG. 3 is a flowchart of a specific coupling reaction measuring method according to another embodiment of the invention.
Figure 4A:
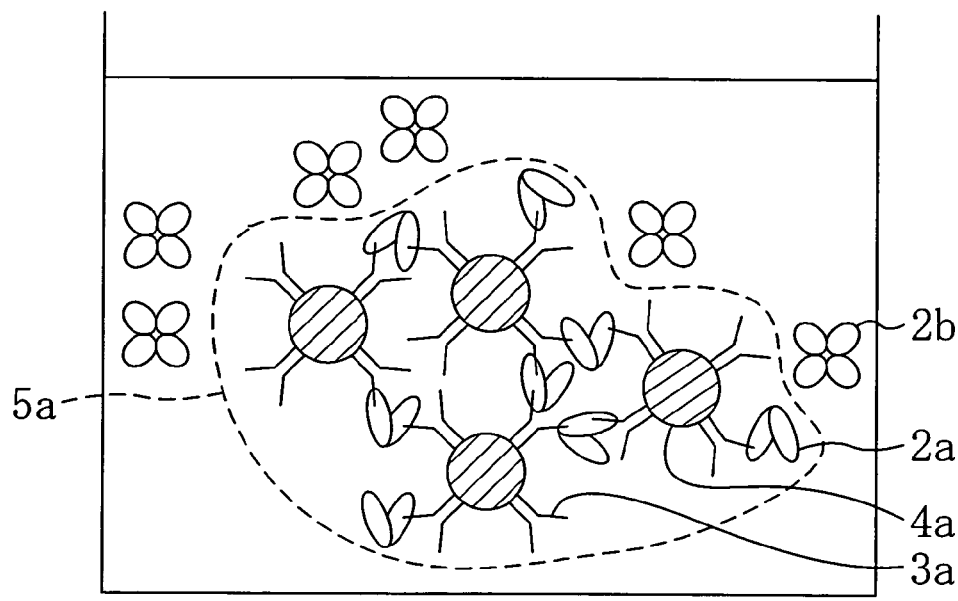
FIGS. 4A and 4B are schematic diagrams of a reaction system in respective procedures in the specific coupling reaction measuring method of FIG. 3.
Figure 4B:
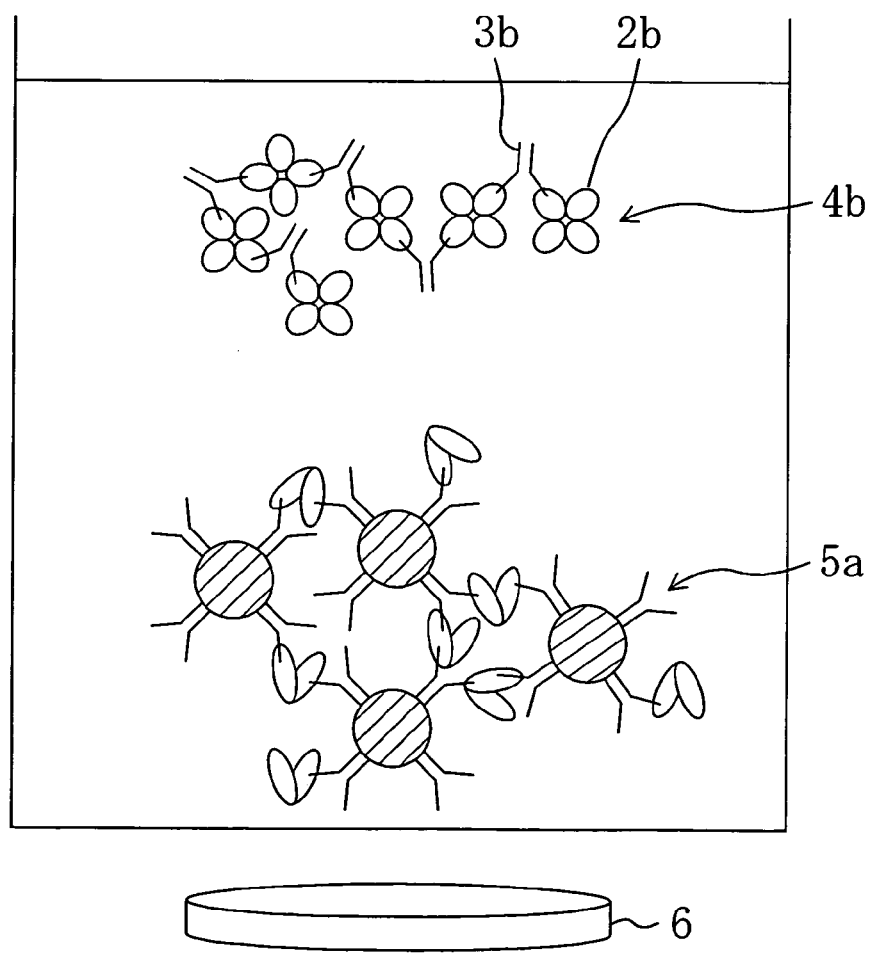

FIG. 3 is a flowchart of the specific coupling reaction measuring method of this embodiment. FIGS. 4A and 4B are schematic diagrams of a reaction system in procedures in the specific coupling reaction measuring method of this embodiment.

First, in step St21 of FIG. 3, a reaction system including a sample in which contents of a first subject substance and a second subject substance are to be measured and a magnetic particle on which a first specific coupling substance for specifically coupling with the first subject substance is immobilized is constructed. The sample can be, for example, a body fluid such as a blood or a urine itself, or a mixture of such a blood fluid and a buffer. In the case where the first subject substance is an antigen, the first specific coupling substance is an antibody, and in the case where the first subject substance is an antibody, the first specific coupling substance is an antigen.

In this manner, when the first subject substance 2a is included in the sample, an agglutination complex 5a including the first subject substance 2a, the first specific coupling substance 3a and the magnetic particle 4a is generated through an antigen-antibody reaction between the first subject substance 2a and the first specific coupling substance 3a as shown in FIG. 4A. When the first subject substance 2a is not included in the sample, the agglutination complex 5a resulting from the antigen-antibody reaction between the first subject substance 2a and the first specific coupling substance 3a is not generated.

Next, in step St22 of FIG. 3, an optical characteristic of the reaction system is measured. At this point, in the case where the agglutination complex 5a has been generated in step St21, turbidity is caused in the reaction system, and hence, the intensity of scattered light and the quantity of transmitted light are changed. Accordingly, the extent of the turbidity of the reaction system can be estimated by measuring the intensity of scattered light or the quantity of transmitted light. At this point, the optical change of the reaction system, namely, the change in the intensity of scattered light or the quantity of transmitted light, is preferably measured with reference to that of the sample obtained before the measurement. When the reaction system is constructed by using the mixture with a buffer as the sample, the buffer may be used as a reference.

Next, in step St23 of FIG. 3, the agglutination complex 5a including the first subject substance 2a, the first specific coupling substance 3a and the magnetic particle 4a and other excessive magnetic particles not forming any agglutination complex 5a are collected by utilizing magnetic force. At this point, the agglutination complex 5a and the excessive magnetic particles may be removed from the reaction system or may be collected in a part of a reaction vessel in which the reaction system is constructed so as not to disturb optical characteristic measurement of the reaction system performed in step St25 described below.

Then, in step St24 of FIG. 3, a second specific coupling substance to be specifically coupled with the second subject substance is added to the reaction system. For example, in the case where the second subject substance is an antigen, the second specific coupling substance is an antibody, and in the case where the second subject substance is an antibody, the second specific coupling substance is an antigen.

In this manner, when the second subject substance is included in the sample, an agglutination complex 4b including the second subject substance 2b and the second specific coupling substance 3b is generated through an antigen-antibody reaction between the second subject substance 2b and the second specific coupling substance 3b as shown in FIG. 4B. Needless to say, when the second subject substance 2b is not included in the sample, the agglutination complex 4b resulting from the antigen-antibody reaction between the second subject substance 2b and the second specific coupling substance 3b is not generated.

Next, in step St25 of FIG. 3, an optical characteristic of the reaction system is measured. At this point, in the case where the agglutination complex 4b has been generated in step St24, turbidity is caused in the reaction system, and hence, the intensity of scattered light and the quantity of transmitted light are changed. Accordingly, the extent of the turbidity of the reaction system can be estimated by measuring the intensity of scattered light or the quantity of transmitted light. At this point, the optical change of the reaction system, namely, the change in the intensity of scattered light or the quantity of transmitted light, is preferably measured with reference to that of the sample obtained before the measurement. When the reaction system is constructed by using the mixture with a buffer as the sample, the buffer may be used as a reference.

Particularly, since the agglutination complex 5a and the excessive magnetic particles not forming any agglutination complex 5a are colleted by utilizing the magnetic force in step St23 as shown in FIG. 4B, when the optical characteristic of the reaction system is measured in this step, the change in the intensity of scattered light and the quantity of transmitted light caused by the agglutination complex 4b alone can be measured.

In particular in this embodiment, in measuring the second subject substance 2b, the excessive magnetic particles 4a present in the reaction system and the change in the optical characteristic of the reaction system caused by the agglutination complex 5a including the first subject substance 2a, the first specific coupling substance 3a and the magnetic particle 4 have been removed from the reaction system by utilizing the magnetic force. Since the magnetic force is used in this embodiment, the reaction system is not chemically affected at all. Therefore, the specific coupling reaction measuring method of this embodiment can attain high reliability in a measured value also in measuring the second subject substance 2b.

In the conventional technique to measure two kinds of subject substances, it is necessary to prepare two reaction vessels according to the number of kinds of subject substances. In contrast, according to this embodiment, merely one reaction vessel in which a reaction system can be constructed can be used for measuring two kinds of subject substances. Accordingly, the quantity of a sample necessary for the measurement is very small in this embodiment. As a result, in the field of, for example, the medical care, the quantity of a sample to be drawn from a patient can be reduced, so as to lighten a burden of the patient.

Moreover, the magnetic particle can be collected to be recycled, with the immobilized antibody or antigen having reactivity, from the agglutination complex 5 and the excessive magnetic particles (not shown) removed from the reaction system in this embodiment by inhibiting the antigen-antibody reaction under an acidic condition of pH 3.0 or less. Alternatively, the antigen or antibody immobilized on the magnetic particle can be completely removed through a treatment with a strong acid or alkali and washing with a surfactant, so that the resultant magnetic particle can be used for immobilizing another antibody or antigen.

Next, a reagent kit used in the specific coupling reaction measuring method of this embodiment will be described with reference to FIGS. 4A and 4B.

The reagent kit used in the specific coupling reaction measuring method of this embodiment includes a magnetic particle 4a on which a first specific coupling substance 3a for specifically coupling with a first subject substance 2a is immobilized, and a second specific coupling substance 3b for specifically coupling with a second subject substance 2b.

When the first subject substance 2a is an antigen, the first specific coupling substance 3a is an antibody, and when the first subject substance 2a is an antibody, the first specific coupling substance 3a is an antigen. Also, when the second subject substance 2b is an antigen, the second specific coupling substance 3b is an antibody, and when the second subject substance 2b is an antibody, the second specific coupling substance 3b is an antigen.

When the reagent kit of this embodiment is used in the specific coupling reaction measuring method of this embodiment, the contents of two kinds of subject substances can be measured with merely one reaction vessel in which a reaction system can be constructed. Accordingly, when the reagent kit of this embodiment is used, the quantity of a sample necessary for the measurement can be very small.

In particular, in measuring the second subject substance 2b, the excessive magnetic particles 4a present in the reaction system and the change in the optical characteristic of the reaction system caused by the agglutination complex 5a including the first subject substance 2a, the first specific coupling substance 3a and the magnetic particle 4 have been removed from the reaction system by utilizing the magnetic force. Since the magnetic force is used in this embodiment, the reaction system is not chemically affected at all. Therefore, the specific coupling reaction measuring method using the reagent kit of this embodiment can attain high reliability in a measured value also in measuring the second subject substance 2b.

The magnetic particles 4a used in the specific coupling reaction measuring method and the reagent kit of this embodiment are preferably insoluble in a reaction system. Specific examples of the magnetic particles 4a are ferrite particles, ferrite colloid particles and ferrite-containing latex particles. Such magnetic particles can be prepared by a user. In particular, magnetic particles having substantially uniform diameters can be obtained as follows: Magnetic bacteria somatically including magnetic particles of 0.05 through 0.1 µm are cultured to increase the number of bacteria; the resultant bacteria are spalled with a French press or the like; and the magnetic particles of the bacteria are collected by using a magnet to be separately taken out. The method for obtaining the magnetic particles from the magnetic bacteria is more specifically described in Japanese Laid-Open Patent Publication No. 2000-346843.

The magnetic particle obtained from the magnetic bacterium is covered with a lipid bilayer. Therefore, such magnetic particles are well dispersed in an aqueous solution or the like and are suitably used for immobilizing a protein such as an antibody used as the specific coupling substance.

The diameter of the magnetic particle 4a used in this embodiment is preferably 0.05 through 2 µm because magnetic particles with such a diameter can be easily homogeneously dispersed in an aqueous solution and can allow the change in the intensity of scattered light or the quantity of transmitted light to be detected for determining the agglutination complex generated through the antigen-antibody reaction.

A magnet 6 is used for generating the magnetic force to collect the magnetic particles in this embodiment, and the magnet 6 is more specifically a permanent magnet or an electromagnet.

In the specific coupling reaction measuring method and the reagent kit of this embodiment, the second specific coupling substance 3b is, for example, an antigen or an antibody but is not limited to this. In particular, the second specific coupling substance 3b is preferably a nonmagnetic particle on which an antigen or an antibody to be antigen-antibody reactive with the second subject substance 2b is immobilized. Thus, in measuring the second subject substance 2b (namely, in step St25), the range in the change of the optical characteristic is not largely varied from the range in the change of the optical characteristic attained in measuring the first subject substance 2a (namely, in step St22). Therefore, an apparatus used for the measurement can be easily adjusted. The nonmagnetic particle is preferred also because the progress of the antigen-antibody reaction of the second subject substance 2b is thus not affected by the magnetic force at all.

Examples of the nonmagnetic particle are glass particles, graphite particles, gold colloid particles and latex particles. Among these particles, the latex particles are preferred because they are highly stable and various diameters are easily available, and preferable latex particles are polystyrene latex particles good at adsorption to a protein.

The nonmagnetic particle is required to be easily dispersed homogeneously in a solution and to allow the change in the intensity of scattered light and the quantity of transmitted light to be detected for determining the agglutination complex generated through the antigen-antibody reaction. Accordingly, the diameter of the nonmagnetic particle is preferably 0.05 through 2 µm, and more preferably equivalent to the diameter of the magnetic particle 4a because the range in the change of the optical characteristic can be thus equivalent to that attained in the measurement using the magnetic particle 4a.

The reaction system used in the specific coupling reaction measuring method of this embodiment may additionally include an arbitrary known component in accordance with the application. For example, in the case where the second specific coupling substance 3b is not a nonmagnetic particle on which an antigen or an antibody is immobilized, polyethylene glycol may be added to the reaction system in step St24. Also, in order to add polyethylene glycol to the reaction system in step St24, the polyethylene glycol may be included in the reagent kit. The content of the polyethylene glycol is preferably 2 through 6 wt % and more preferably 4 wt % with respect to the reaction system. In the case where the polyethylene glycol is included in the reaction system in the aforementioned concentration, nonspecific agglutination through autoagglutinin of the second subject substance 2b and the second specific coupling substance 3b can be reduced, so as to improve the measurement sensitivity.

Furthermore, in order to reduce the nonspecific agglutination through autoagglutinin of the first subject substance 2a, the first specific coupling substance 3a, the second subject substance 2b and the second specific coupling substance 3b, a surfactant such as Tween 20, octyl glucoside, sodium lauryl sulfate (SDS), sucrose monolaurate or CHAPS may be added to the reaction system in step St22 and step St25 of this embodiment. The content of the surfactant in the reaction system is preferably 0.3 wt % or less and more preferably 0.1 wt % or less because the surfactant of such a content minimally affects the antigen-antibody reaction.

In the specific coupling reaction measuring method of this embodiment, as the optical characteristic measured in step St22 and step St25, change in the intensity of scattered light may be measured (as in the nephelometry) or change in the quantity of transmitted light may be measured (as in the turbidimetry).

The first subject substance 2a and the second subject substance 2b of this embodiment are not particularly specified but may be any substance that can be measured by utilizing an antigen-antibody reaction. Examples of the subject substance are protein, nucleic acid, lipid, bacteria, virus and hapten. In particular, the specific coupling reaction measuring method and the reagent kit of this embodiment are suitably used for measuring a protein that is conventionally measured by utilizing an antigen-antibody reaction in the clinical examination. Examples of the protein are hormones such as LH (luteinzing hormone), FSH (follicle-stimulating hormone) and hCG (human chorionic gonadotropin), various immunoglobulin classes and sub-classes, a component of complement, markers of various infectious diseases, CRP, albumin, hemoglobin, rheumatoid factors and blood group antigens. For example, when the first subject substance 2a and the second subject substance 2b of this embodiment are human hemoglobin and human albumin, respectively, this embodiment can provide measurement results suitable to initial screening for a kidney disease. This is because the measurement result of human urinary hemoglobin can be used as an index of inflammation, calculosis or a tumor of a urinary tract such as acute glomerulonephritis, IgA nephropathy, nephrophthisis, renal infarction, interstitial nephritis, cystitis, urethritis or prostatitis and the measurement result of human urinary albumin is easily affected by change in the total quantity of proteins in a urine, so that the function of a kidney can be evaluated on the basis of these measurement results.

The antibody used in this embodiment is not particularly specified as far as it can produce an agglutination complex together with an antigen by specifically coupling with the antigen. Examples of the antibody are antibodies of any antibody class of IgG, IgM, IgE, IgA or IgD, and a mixture of any of these antibodies. Also, the antibody may be a polyclonal antibody or a monoclonal antibody, or a mixture of them. Among these antibodies, IgG antibodies are preferred because they are less nonspecifically reacted and are comparatively easily commercially available and hence are easily obtained. Also, the kind of original animal of the antibody is not particularly specified, and antibodies derived from a rabbit, a goat and a mouse are preferred because they are comparatively easily obtained and widely used.

Although an immune reaction measuring method utilizing an antigen-antibody reaction is described as a specific coupling reaction measuring method in this embodiment, the measurement can be performed by generating an agglutination complex by using another reaction for causing specific coupling other than the antigen-antibody reaction. When another reaction for causing specific coupling other than the antigen-antibody reaction is used, a combination of a subject substance and a specific coupling substance can be, for example, a combination of a ligand and a receptor or a combination of a single-stranded DNA (subject substance) and various DNA fragments (specific coupling substance) having complementary sequences of the single-stranded DNA.

An example of the combination of a ligand and a receptor is a combination of a molecule working as a ligand and an allosteric protein having a plurality of coupling sites with the molecule. In the case where the molecule working as a ligand has merely one site to be coupled with an allosteric protein, an agglutination complex including the molecule working as a ligand and the allosteric protein can be generated by immobilizing the molecule working as a ligand on a magnetic particle or a nonmagnetic particle with a site other than that to be coupled with the allosteric protein.

Alternatively, in the case of a single-stranded DNA (subject substance) and various DNA fragments (specific coupling substance) having complementary sequences of the single-stranded DNA, so as to form agglutination complex, the various DNA fragments may be immobilized on a magnetic particle or a nonmagnetic particle so as to be complementarily capable of coupling with the single-stranded DNA.

EMBODIMENT 3

In Embodiment 3 of the invention, a specific coupling reaction measuring method for measuring the contents of a further larger number of kinds of subject substances, which results from expansion of the specific coupling reaction measuring method of Embodiment 2, will be described with reference to the accompanying drawing.

FIG. 5 is a flowchart of the specific coupling reaction measuring method of this embodiment.

First, in step St31 of FIG. 5, a reaction system including a sample in which contents of n kinds (wherein n is an integer of 2 or more) of subject substances are to be measured and a magnetic particle on which a specific coupling substance for specifically coupling with one of the subject substances is immobilized is constructed. The sample can be, for example, a body fluid such as a blood or a urine itself, or a mixture of such a body fluid and a buffer. In the case where the subject substance is an antigen, the specific coupling substance is an antibody, and in the case where the subject substance is an antibody, the specific coupling substance is an antigen.

In this manner, when the subject substance is included in the sample, an agglutination complex including the subject substance, the specific coupling substance and the magnetic particle, which is equivalent to the agglutination complex 5a shown in FIG. 4A of Embodiment 2, is generated through an antigen-antibody reaction between the subject substance and the specific coupling substance. When the subject substance is not included in the sample, the agglutination complex resulting from the antigen-antibody reaction between the subject substance and the specific coupling substance is not generated.

Next, in step St32 of FIG. 5, an optical characteristic of the reaction system is measured. At this point, in the case where the agglutination complex has been generated in step St31, turbidity is caused in the reaction system, and hence, the intensity of scattered light and the quantity of transmitted light are changed. Accordingly, the extent of the turbidity of the reaction system can be estimated by measuring the intensity of scattered light or the quantity of transmitted light. At this point, the optical change of the reaction system, namely, the change in the intensity of scattered light or the quantity of transmitted light, is preferably measured with reference to that of the sample obtained before the measurement. When the reaction system is constructed by using the mixture with a buffer as the sample, the buffer may be used as a reference.

Next, in step St33 of FIG. 5, the agglutination complex including the subject substance, the specific coupling substance and the magnetic particle and other excessive magnetic particles not forming any agglutination complex are removed from the reaction system by utilizing magnetic force.

Then, in step St34 of FIG. 5, it is determined whether or not step St32 has been repeated (n−1) times. When it is determined that step St32 has been repeated (n−1) times, the flow proceeds to step St35. When it is determined that step St32 has not been repeated (n−1) times, the flow returns to step St31. In other words, the procedures in steps St31 through St33 are repeatedly performed until step St32 is repeated (n−1) times. Through these repeated procedures, among the n kinds of subject substances, (n−1) kinds of subject substances are removed from the reaction system.

Next, in step St35 of FIG. 5, a specific coupling substance to be specifically coupled with one remaining subject substance not measured yet in the reaction system is added to the reaction system. At this point, for example, in the case where the subject substance is an antigen, the specific coupling substance is an antibody, and in the case where the subject substance is an antibody, the specific coupling substance is an antigen.

In this manner, when the subject substance is included in the sample, an agglutination complex including the subject substance and the specific coupling substance, which is equivalent to the agglutination complex 4b shown in FIG. 4B of Embodiment 2, is generated through an antigen-antibody reaction between the subject substance and the specific coupling substance. Needless to say, when the subject substance is not included in the sample, the agglutination complex resulting from the antigen-antibody reaction between the subject substance and the specific coupling substance is not generated.

Next, in step St36 of FIG. 5, an optical characteristic of the reaction system is measured. At this point, in the case where the agglutination complex has been generated in step St35, turbidity is caused in the reaction system, and hence, the intensity of scattered light and the quantity of transmitted light are changed. Accordingly, the extent of the turbidity of the reaction system can be estimated by measuring the intensity of scattered light or the quantity of transmitted light. At this point, the optical change of the reaction system, namely, the change in the intensity of scattered light or the quantity of transmitted light, is preferably measured with reference to that of the sample obtained before the measurement. When the reaction system is constructed by using the mixture with a buffer as the sample, the buffer may be used as a reference.

Particularly, since the agglutination complex and the excessive magnetic particles not forming any agglutination complex are colleted by utilizing the magnetic force in step St33, when the optical characteristic of the reaction system is measured in this step, change in the intensity of scattered light and the quantity of transmitted light caused by the agglutination complex alone can be measured.

In this embodiment, the agglutination complex including the subject substance, the specific coupling substance and the magnetic particle is removed after the measurement of the optical characteristic by utilizing the magnetic force. Since the magnetic force is used, the reaction system is not chemically affected at all. Therefore, in measuring a plurality of subject substances, the influences of previously generated agglutination complexes are substantially eliminated, and hence, every measurement of the optical characteristic can attain high reliability in a measured value.

In particular in the conventional technique to measure two or more kinds of subject substances, it is necessary to prepare reaction vessels in the same number as the number of kinds of subject substances. In contrast, according to this embodiment, merely one reaction vessel in which a reaction system can be constructed can be used for measuring two or more kinds of subject substances. Accordingly, the quantity of a sample necessary for the measurement is very small in this embodiment. As a result, in the field of, for example, the medical care, the quantity of a sample to be drawn from a patient can be reduced, so as to lighten a burden of the patient.

Moreover, the magnetic particle can be collected to be recycled, with the immobilized antibody or antigen having reactivity, from the agglutination complex 5 and the excessive magnetic particles (not shown) removed from the reaction system in this embodiment by inhibiting the antigen-antibody reaction under an acidic condition of pH 3.0 or less. Alternatively, the antigen or antibody immobilized on the magnetic particle can be completely removed through a treatment with a strong acid or alkali and washing with a surfactant, so that the resultant magnetic particle can be used for immobilizing another antibody or antigen.

Next, a reagent kit used in the specific coupling reaction measuring method of this embodiment will be described.

The reagent kit used in the specific coupling reaction measuring method of this embodiment includes magnetic particles on which specific coupling substances for respectively specifically coupling with the (n−1) kinds of subject substances are respectively immobilized, and a specific coupling substance for specifically coupling with remaining one kind of subject substance.

When the reagent kit of this embodiment is used in the specific coupling reaction measuring method of this embodiment, the contents of two or more kinds of subject substances can be measured with merely one reaction vessel in which a reaction system can be constructed. Accordingly, when the reagent kit of this embodiment is used, the quantity of a sample necessary for the measurement can be very small.

The magnetic particles and a magnet 6 for collecting the magnetic particles used in the specific coupling reaction measuring method and the reagent kit of this embodiment can be the same as those described in Embodiment 2.

In the specific coupling reaction measuring method and the reagent kit of this embodiment, the specific coupling substance added in step St35 of FIG. 5 is preferably a nonmagnetic particle on which an antigen or an antibody to be antigen-antibody reactive with the one remaining subject substance not measured yet in the reaction system is immobilized. Thus, the range in the change of the optical characteristic attained in step St36 is not largely varied from the ranges in the changes of the optical characteristics of the (n−1) kinds of subject substances attained in step St32. Therefore, an apparatus used for the measurement can be easily adjusted.

The nonmagnetic particle can be the same as that described in Embodiment 2. Specifically, the diameter of the nonmagnetic particle is preferably 0.05 through 2 μm and more preferably equivalent to the diameter of the magnetic particle.

The reaction system used in the specific coupling reaction measuring method of this embodiment may additionally include an arbitrary known component in accordance with the application. For example, in the case where the specific coupling substance is not a nonmagnetic particle on which an antigen or an antibody is immobilized, polyethylene glycol may be added to the reaction system in step St35. Also, in order to add polyethylene glycol to the reaction system in step St35, the polyethylene glycol may be included in the reagent kit. The content of the polyethylene glycol is preferably 2 through 6 wt % and more preferably 4 wt % with respect to the reaction system. In the case where the polyethylene glycol is included in the reaction system in the aforementioned concentration, nonspecific agglutination through autoagglutinin of the subject substances and the specific coupling substances can be reduced in step St36, so as to improve the measurement sensitivity.

Furthermore, in order to reduce the nonspecific agglutination through autoagglutinin of the respective subject substances and the respective specific coupling substances, a surfactant such as Tween 20, octyl glucoside, sodium lauryl sulfate (SDS), sucrose monolaurate or CHAPS may be added to the reaction system in steps St32 and St36. The content of the surfactant in the reaction system is preferably 0.3 wt %/o or less and more preferably 0.1 wt % or less because the surfactant of such a content minimally affects an antigen-antibody reaction.

In the specific coupling reaction measuring method of this embodiment, as the optical characteristic measured in step St32 and step St36, change in the intensity of scattered light may be measured (as in the nephelometry) or change in the quantity of transmitted light may be measured (as in the turbidimetry).

The n kinds of subject substances of this embodiment are not particularly specified but may be any substance that can be measured by utilizing an antigen-antibody reaction. Examples of the subject substance are protein, nucleic acid, lipid, bacteria, virus and hapten. In particular, the specific coupling reaction measuring method and the reagent kit of this embodiment are suitably used for measuring a protein that is conventionally measured by utilizing an antigen-antibody reaction in the clinical examination. Examples of the protein are hormones such as LH (luteinzing hormone), FSH (follicle-stimulating hormone) and hCG (human chorionic gonadotropin), various immunoglobulin classes and sub-classes, a component of complement, markers of various infectious diseases, CRP, albumin, hemoglobin, rheumatoid factors and blood group antigens.

The antibody used in this embodiment is not particularly specified as far as it can produce an agglutination complex together with an antigen by specifically coupling with the antigen. Examples of the antibody are antibodies of any antibody class of IgG, IgM, IgE, IgA or IgD, and a mixture of any of these antibodies. Also, the antibody may be a polyclonal antibody or a monoclonal antibody, or a mixture of them. Among these antibodies, IgG antibodies are preferred because they are less nonspecifically reacted and are comparatively easily commercially available and hence are easily obtained. Also, the kind of original animal of the antibody is not particularly specified, and antibodies derived from a rabbit, a goat and a mouse are preferred because they are comparatively easily obtained and widely used.

Although an immune reaction measuring method utilizing an antigen-antibody reaction is described as a specific coupling reaction measuring method in this embodiment, the measurement can be performed by generating an agglutination complex by using another reaction for causing specific coupling other than the antigen-antibody reaction. When another reaction for causing specific coupling other than the antigen-antibody reaction is used, a combination of a subject substance and a specific coupling substance can be, for example, a combination of a ligand and a receptor or a combination of a single-stranded DNA (subject substance)

and various DNA fragments (specific coupling substance) having complementary sequences of the single-stranded DNA.

An example of the combination of a ligand and a receptor is a combination of a molecule working as a ligand and an allosteric protein having a plurality of coupling sites with the molecule. In the case where the molecule working as a ligand has merely one site to be coupled with an allosteric protein, an agglutination complex including the molecule working as a ligand and the allosteric protein can be generated by immobilizing the molecule working as a ligand on a magnetic particle or a nonmagnetic particle with a site other than that to be coupled with the allosteric protein.

Alternatively, in the case of a single-stranded DNA (subject substance) and various DNA fragments (specific coupling substance) having complementary sequences of the single-stranded DNA, so as to form agglutination complex, the various DNA fragments may be immobilized on a magnetic particle or a nonmagnetic particle so as to be complementarily capable of coupling with the single-stranded DNA.

EMBODIMENT 4

In Embodiment 4 of the invention, another specific coupling reaction measuring method for measuring the contents of a larger number of kinds of subject substances will be described with reference to the accompanying drawings.

Figure 6:
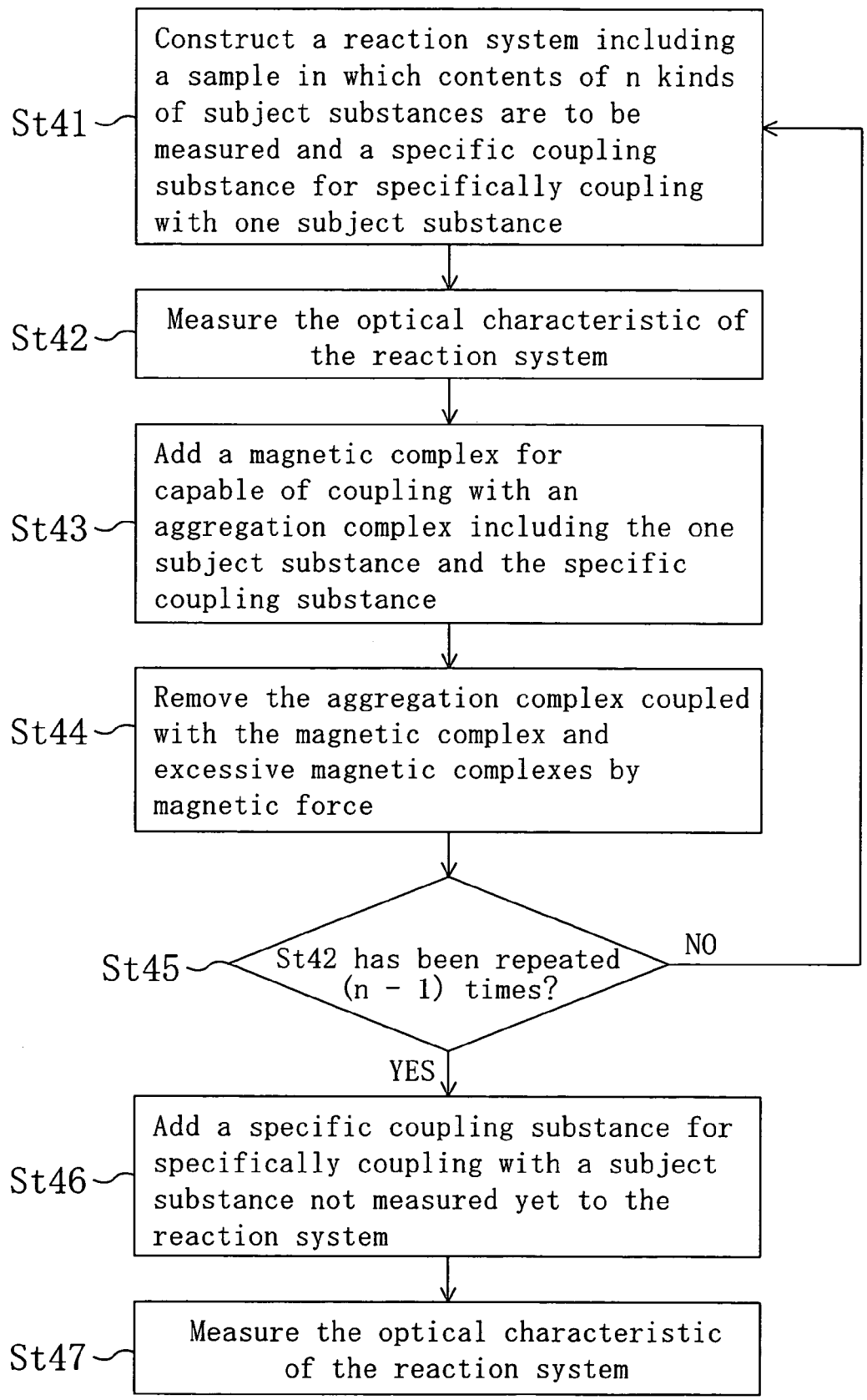
FIG. 6 is a flowchart of a specific coupling reaction measuring method according to still another embodiment of the invention.
Figure 7A:
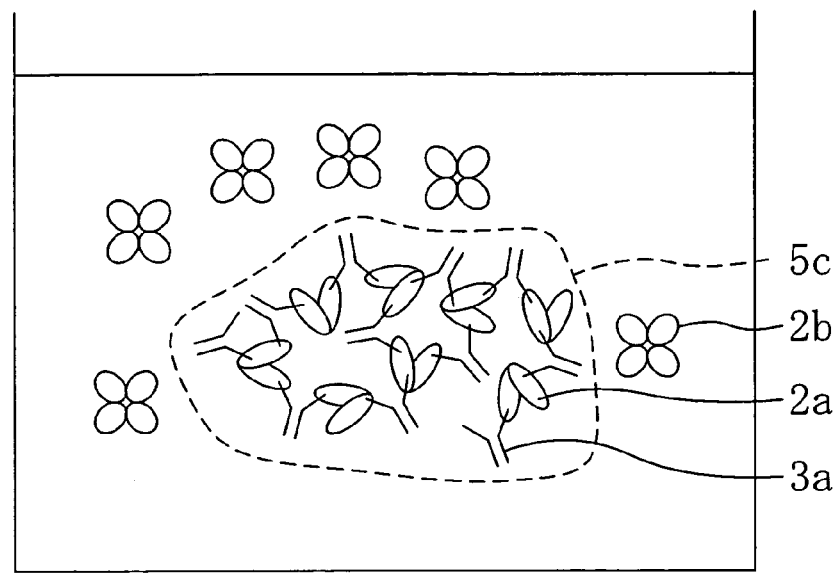
FIGS. 7A and 7B are schematic diagrams of a reaction system in respective procedures in the specific coupling reaction measuring method of FIG. 6.
Figure 7B:
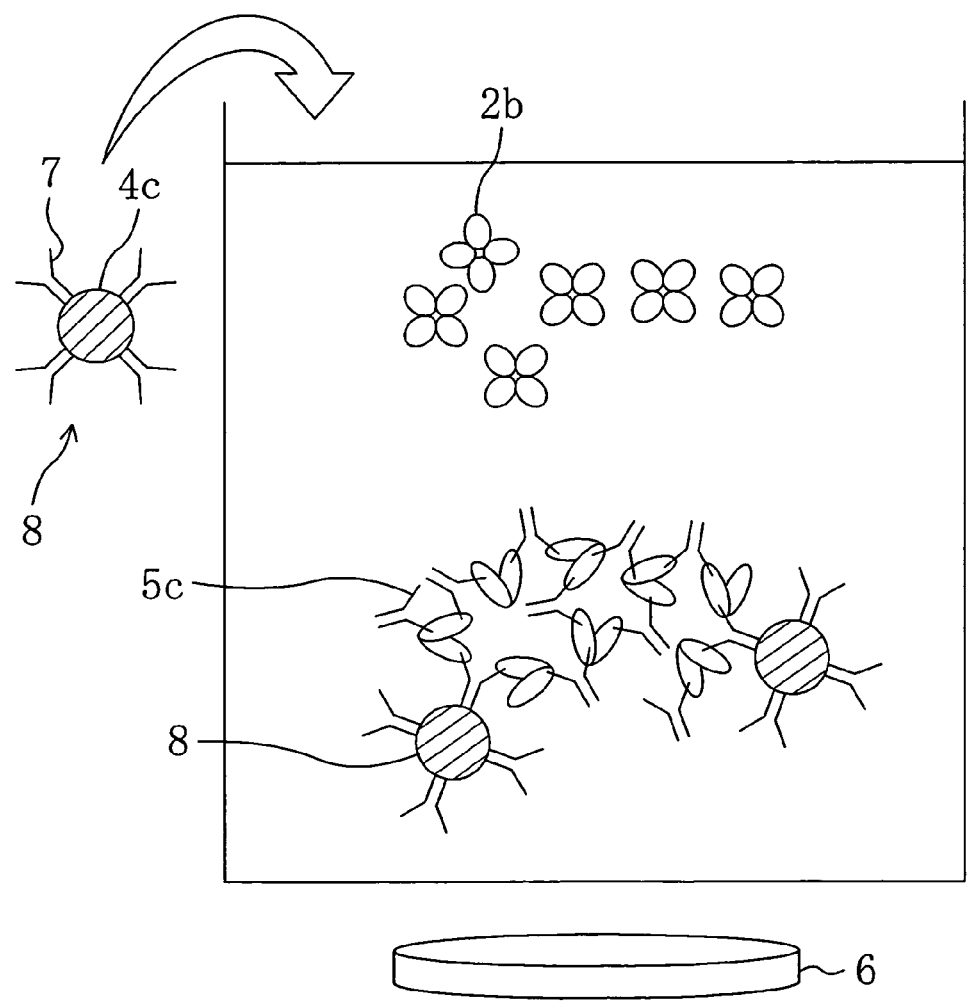

FIG. 6 is a flowchart of the specific coupling reaction measuring method of this embodiment. FIGS. 7A and 7B are schematic diagrams of a reaction system in procedures in the specific coupling reaction measuring method of this embodiment.

First, in step St41 of FIG. 6, a reaction system including a sample in which contents of n kinds (wherein n is an integer of 2 or more) of subject substances are to be measured and a specific coupling substance for specifically coupling with one of the subject substances not measured yet is constructed. The sample can be, for example, a body fluid such as a blood or a urine itself, or a mixture of such a body fluid and a buffer. In the case where the subject substance is an antigen, the specific coupling substance is an antibody, and in the case where the subject substance is an antibody, the specific coupling substance is an antigen.

In this manner, when the subject substance is included in the sample, an agglutination complex 5c including the subject substance 2a and the specific coupling substance 3a is generated through an antigen-antibody reaction between the subject substance 2a and the specific coupling substance 3a as shown in FIG. 7A. When the subject substance 2a is not included in the sample, the agglutination complex 5c resulting from the antigen-antibody reaction between the subject substance 2a and the specific coupling substance 3a is not generated.

Next, in step St42 of FIG. 6, an optical characteristic of the reaction system is measured. At this point, in the case where the agglutination complex has been generated in step St41, turbidity is caused in the reaction system, and hence, the intensity of scattered light and the quantity of transmitted light are changed. Accordingly, the extent of the turbidity of the reaction system can be estimated by measuring the intensity of scattered light or the quantity of transmitted light. At this point, the optical change of the reaction system, namely, the change in the intensity of scattered light or the quantity of transmitted light, is preferably measured with reference to that of the sample obtained before the measurement. Alternatively, when the reaction system is constructed by using the mixture with a buffer as the sample, the buffer may be used as a reference.

Next, in step St43 of FIG. 6, a magnetic complex that includes a magnetic particle and a substance capable of coupling with the agglutination complex including the one subject substance and the specific coupling substance (for example, an antigen capable of coupling with an antigen included in the agglutination complex) is added to the reaction system. Thus, as shown in FIG. 7B, the magnetic complex 8 including the antibody 7 and the magnetic particle 4c is coupled with the agglutination complex 5c.

Then, in step S44 of FIG. 6, the agglutination complex coupled with the magnetic complex and other excessive magnetic complexes not coupled with any agglutination complex are removed by utilizing magnetic force. Thus, the agglutination complex 5c is attracted by the magnetic force together with the magnetic complex 8 to be removed, and another subject substance 2b remains in the reaction system as shown in FIG. 7B.

Then, in step St45 of FIG. 6, it is determined whether or not step St42 has been repeated (n−1) times. When it is determined that step St42 has been repeated (n−1) times, the flow proceeds to step St46. When it is determined that step St42 has not been repeated (n−1) times, the flow returns to step St41. In other words, the procedures in steps St41 through St44 are repeatedly performed until step St42 is repeated (n−1) times. Through these repeated procedures, among the n kinds of subject substances, (n−1) kinds of subject substances are removed from the reaction system.

Next, in step St46 of FIG. 6, a specific coupling substance to be specifically coupled with one remaining subject substance not measured yet in the reaction system is added to the reaction system. At this point, for example, in the case where the subject substance is an antigen, the specific coupling substance is an antibody, and in the case where the subject substance is an antibody, the specific coupling substance is an antigen.

In this manner, when the subject substance is included in the sample, an agglutination complex including the subject substance and the specific coupling substance, which is equivalent to the agglutination complex 4b shown in FIG. 4B of Embodiment 2, is generated through an antigen-antibody reaction between the subject substance and the specific coupling substance. Needless to say, when the subject substance is not included in the sample, the agglutination complex resulting from the antigen-antibody reaction between the subject substance and the specific coupling substance is not generated.

Next, in step St47 of FIG. 6, an optical characteristic of the reaction system is measured. At this point, in the case where the agglutination complex has been generated in step St46, turbidity is caused in the reaction system, and hence, the intensity of scattered light and the quantity of transmitted light are changed. Accordingly, the extent of the turbidity of the reaction system can be estimated by measuring the intensity of scattered light or the quantity of transmitted light. At this point, the optical change of the reaction system, namely, the change in the intensity of scattered light or the quantity of transmitted light, is preferably measured with reference to that of the sample obtained before the measurement. When the reaction system is constructed by using the mixture with a buffer as the sample, the buffer may be used as a reference.

Particularly, since the agglutination complex and the magnetic complex are colleted by utilizing the magnetic force in step St44, when the optical characteristic of the reaction system is measured in this step, change in the intensity of scattered light and the quantity of transmitted light caused by the agglutination complex alone can be measured.

In this embodiment, the agglutination complex including the subject substance and the specific coupling substance are removed after the measurement of the optical characteristic by utilizing the magnetic force. Since the magnetic force is used, the reaction system is not chemically affected at all. Therefore, in measuring a plurality of subject substances, the influences of previously generated agglutination complexes are substantially eliminated, and hence, every measurement of the optical characteristic can attain high reliability in a measured value.

In particular in the conventional technique to measure two or more kinds of subject substances, it is necessary to prepare reaction vessels in the same number as the number of kinds of subject substances. In contrast, according to this embodiment, merely one reaction vessel in which a reaction system can be constructed can be used for measuring two or more kinds of subject substances. Accordingly, the quantity of a sample necessary for the measurement is very small in this embodiment. As a result, in the field of, for example, the medical care, the quantity of a sample to be drawn from a patient can be reduced, so as to lighten a burden of the patient.

Moreover, the magnetic particle can be collected to be recycled, with the immobilized antibody or antigen having reactivity, from the agglutination complex 5 and the excessive magnetic particles (not shown) removed from the reaction system in this embodiment by inhibiting the antigen-antibody reaction under an acidic condition of pH 3.0 or less. Alternatively, the antigen or antibody immobilized on the magnetic particle can be completely removed through a treatment with a strong acid or alkali and washing with a surfactant, so that the resultant magnetic particle can be used for immobilizing another antibody or antigen.

Next, a reagent kit used in the specific coupling reaction measuring method of this embodiment will be described.

The reagent kit used in the specific coupling reaction measuring method of this embodiment includes specific coupling substances for respectively specifically coupling with the n kinds of subject substances, and magnetic complexes respectively including substances respectively capable of coupled with agglutination complexes each including each of the (n−1) kinds of subject substances and corresponding specific coupling substances and magnetic particles on which the substances are respectively immobilized.

When the reagent kit of this embodiment is used in the specific coupling reaction measuring method of this embodiment, the contents of two or more kinds of subject substances can be measured with merely one reaction vessel in which a reaction system can be constructed. Accordingly, when the reagent kit of this embodiment is used, the quantity of a sample necessary for the measurement can be very small.

The magnetic particles and a magnet 6 for collecting the magnetic particles used in the specific coupling reaction measuring method and the reagent kit of this embodiment can be the same as those described in Embodiment 2.

As the magnetic complex for specifically coupling with the agglutination complex used in this embodiment can be a magnetic particle on which an antibody for specifically coupling with the antibody forming each agglutination complex, an antibody specifically coupling with a different site from the antibody forming each agglutination complex or an antibody specifically coupled with a specific structure of each agglutination complex is immobilized.

In the specific coupling reaction measuring method and the reagent kit of this embodiment, the specific coupling substance added in step St46 of FIG. 6 is preferably a nonmagnetic particle on which an antigen or an antibody to be antigen-antibody reactive with the one remaining subject substance not measured yet in the reaction system is immobilized. Thus, the range in the change of the optical characteristic attained in step St47 is not largely varied from the ranges in the changes of the optical characteristics of the (n−1) kinds of subject substances attained in step St42. Therefore, an apparatus used for the measurement can be easily adjusted.

The nonmagnetic particle can be the same as that described in Embodiment 2. Specifically, the diameter of the nonmagnetic particle is preferably 0.05 through 2 μm and more preferably equivalent to the diameter of the magnetic particle.

The reaction system used in the specific coupling reaction measuring method of this embodiment may additionally include an arbitrary known component in accordance with the application. For example, in the case where the specific coupling substance is not a nonmagnetic particle on which an antigen or an antibody is immobilized, polyethylene glycol may be added to the reaction system in step St46. Also, in order to add polyethylene glycol to the reaction system in step St46, the polyethylene glycol may be included in the reagent kit. The content of the polyethylene glycol is preferably 2 through 6 wt % and more preferably 4 wt % with respect to the reaction system. In the case where the polyethylene glycol is included in the reaction system in the aforementioned concentration, nonspecific agglutination through autoagglutinin of the subject substance and the specific coupling substance can be reduced in step St47, so as to improve the measurement sensitivity.

Furthermore, in order to reduce the nonspecific agglutination through autoagglutinin of the respective subject substances and the respective specific coupling substances, a surfactant such as Tween 20, octyl glucoside, sodium lauryl sulfate (SDS), sucrose monolaurate or CHAPS may be added to the reaction system in steps St42 and St47. The content of the surfactant in the reaction system is preferably 0.3 wt % or less and more preferably 0.1 wt % or less because the surfactant of such a content minimally affects an antigen-antibody reaction.

In the specific coupling reaction measuring method of this embodiment, as the optical characteristic measured in step St42 and step St47, change in the intensity of scattered light may be measured (as in the nephelometry) or change in the quantity of transmitted light may be measured (as in the turbidimetry).

The n kinds of subject substances of this embodiment are not particularly specified but may be any substance that can be measured by utilizing an antigen-antibody reaction. Examples of the subject substance are protein, nucleic acid, lipid, bacteria, virus and hapten. In particular, the specific coupling reaction measuring method and the reagent kit of this embodiment are suitably used for measuring a protein that is conventionally measured by utilizing an antigen-antibody reaction in the clinical examination. Examples of the protein are hormones such as LH (luteinzing hormone), FSH (follicle-stimulating hormone) and hCG (human chorionic gonadotropin), various immunoglobulin classes and sub-classes, a component of complement, markers of various infectious diseases, CRP, albumin, hemoglobin, rheumatoid factors and blood group antigens.

The antibody used in this embodiment is not particularly specified as far as it can produce an agglutination complex together with an antigen by specifically coupling with the antigen. Examples of the antibody are antibodies of any antibody class of IgG, IgM, IgE, IgA or IgD, and a mixture of any of these antibodies. Also, the antibody may be a polyclonal antibody or a monoclonal antibody, or a mixture of them. Among these antibodies, IgG antibodies are preferred because they are less nonspecifically reacted and are comparatively easily commercially available and hence are easily obtained. Also, the kind of original animal of the antibody is not particularly specified, and antibodies derived from a rabbit, a goat and a mouse are preferred because they are comparatively easily obtained and widely used.

Although an immune reaction measuring method utilizing an antigen-antibody reaction is described as a specific coupling reaction measuring method in this embodiment, the measurement can be performed by generating an agglutination complex by using another reaction for causing specific coupling other than the antigen-antibody reaction. When another reaction for causing specific coupling other than the antigen-antibody reaction is used, a combination of a subject substance and a specific coupling substance can be, for example, a combination of a ligand and a receptor or a combination of a single-stranded DNA (subject substance) and various DNA fragments (specific coupling substance) having complementary sequences of the single-stranded DNA.

An example of the combination of a ligand and a receptor is a combination of a molecule working as a ligand and an allosteric protein having a plurality of coupling sites with the molecule. In the case where the molecule working as a ligand has merely one site to be coupled with an allosteric protein, an agglutination complex including the molecule working as a ligand and the allosteric protein can be generated by immobilizing the molecule working as a ligand on a magnetic particle or a nonmagnetic particle with a site other than that to be coupled with the allosteric protein.

Alternatively, in the case of a single-stranded DNA (subject substance) and various DNA fragments (specific coupling substance) having complementary sequences of the single-stranded DNA, so as to form agglutination complex, the various DNA fragments may be immobilized on a magnetic particle or a nonmagnetic particle so as to be complementarily capable of coupling with the single-stranded DNA.

EMBODIMENT 5

In Embodiment 5 of the invention, a measuring apparatus used for practicing the specific coupling reaction measuring method of any of Embodiments 1 through 4 will be described with reference to the accompanying drawings.

Figure 8:
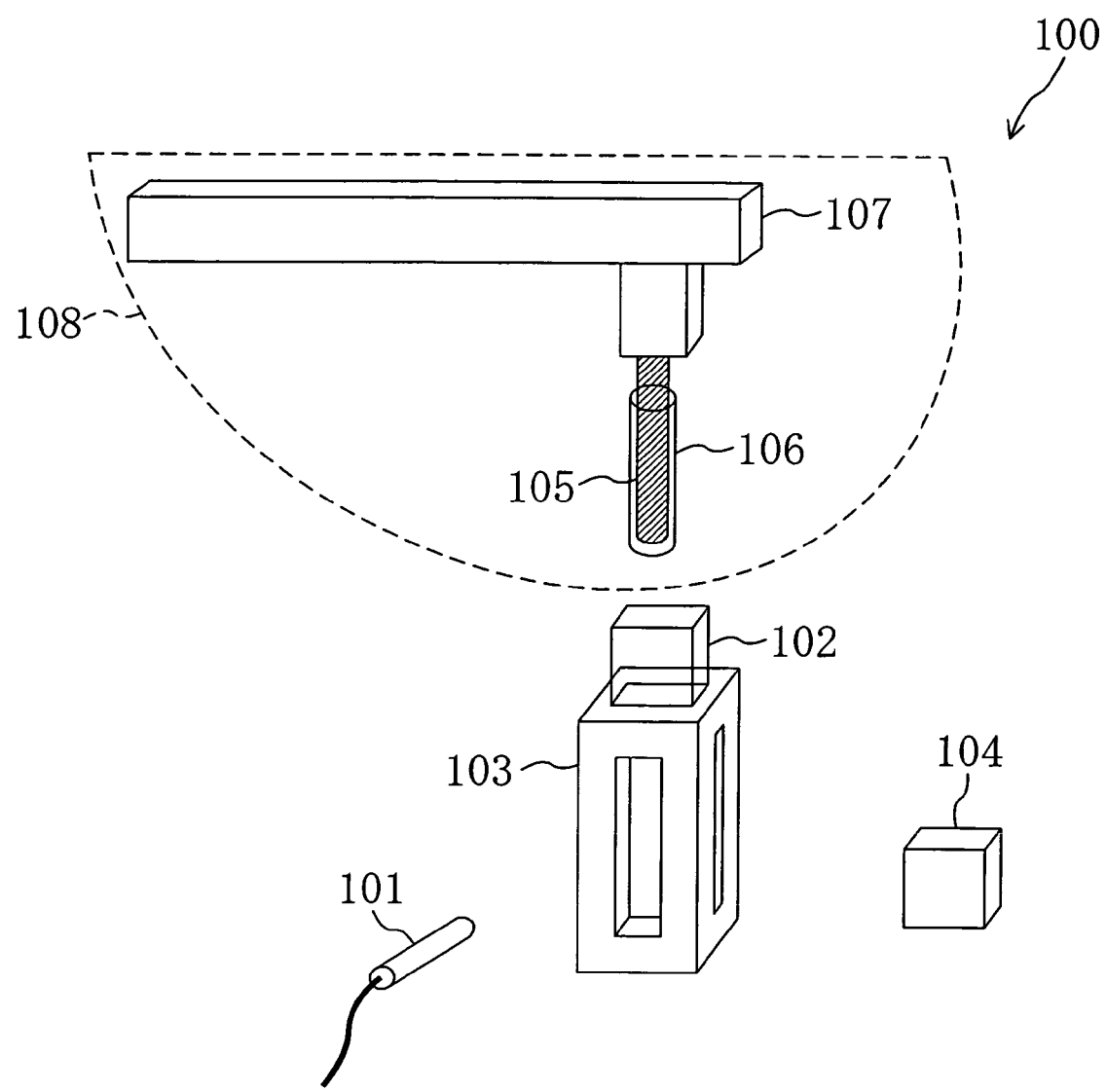
FIG. 8 is a schematic diagram of a measuring apparatus according to an embodiment of the invention.

The measuring apparatus 100 will be first described with reference to FIG. 8. FIG. 8 is a schematic diagram of the measuring apparatus 100 of this embodiment.

The measuring apparatus 100 of this embodiment includes, as shown in FIG. 8, a light source 101, a cell (reaction vessel) 102, a cell holder 103 for holding the cell 102, a photodetector 104 for detecting light received from the cell 102 and a removing section 108.

The light source 101 is disposed so that emitted light can proceed to the cell 102.

The photodetector 104 detects scattered light or transmitted light received from a reaction system constructed within the cell 102.

The removing section 108 is used for collecting and removing, by utilizing magnetic force, a magnetic particle, a magnetic complex or an agglutination complex from the reaction system in each of Embodiments 1 through 4. In the measuring apparatus 100, the removing section 108 includes a permanent magnet 105, a cover 106 for protecting the permanent magnet 105 and an arm 107 on which the permanent magnet 105 and the cover 106 are provided.

Figure 9:
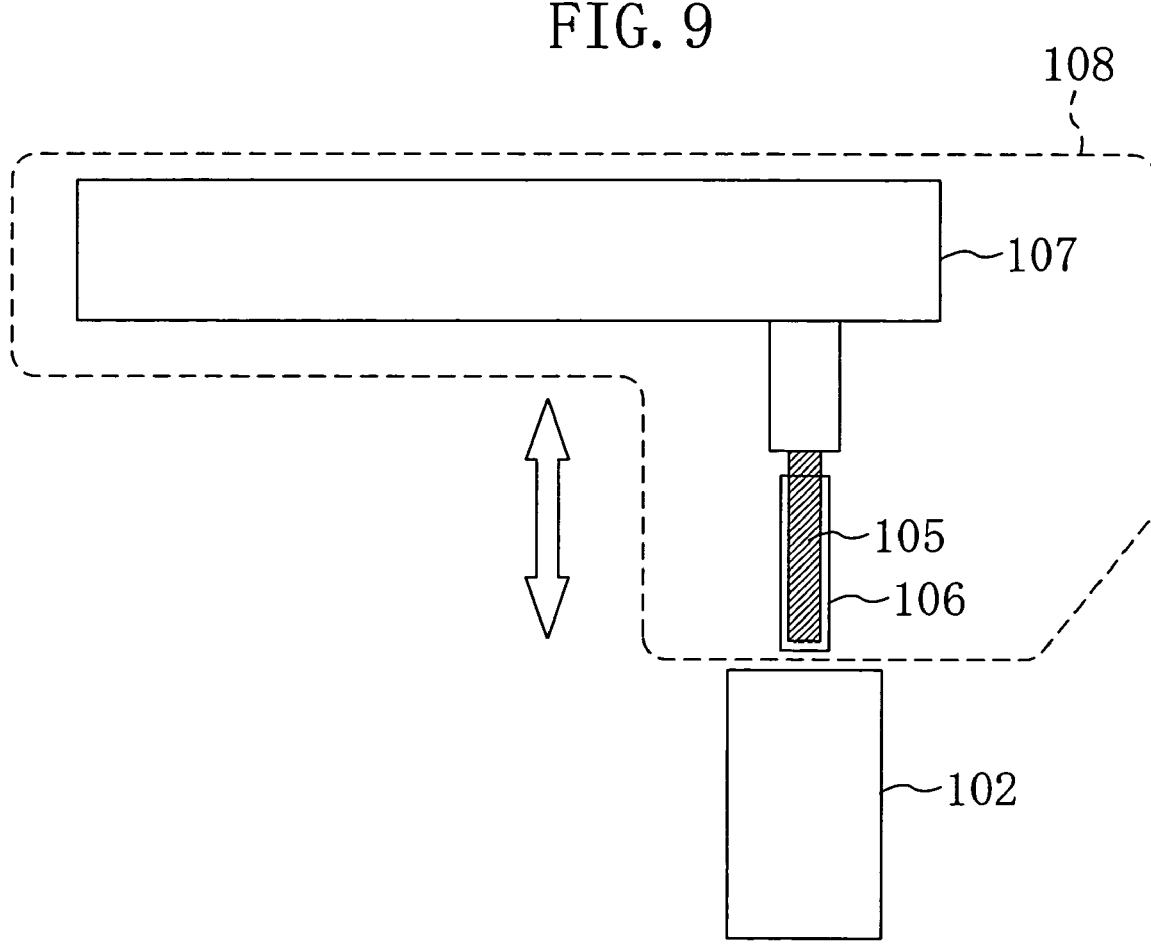
FIG. 9 is a diagram for showing the arrangement relationship in a part of the measuring apparatus of FIG. 8.

Now, the operation of the removing section 108 will be described with reference to FIG. 9. FIG. 9 is a diagram for showing the arrangement relationship between the cell 102 and the removing section 108 in the measuring apparatus 100 of this embodiment.

As shown in FIG. 9, the arm 107 can be lowered to insert the permanent magnet 105 and the cover 106 into the cell 102 and can be elevated to draw up the permanent magnet 105 and the cover 106 from the cell 102. Accordingly, the permanent magnet 105 and the cover 106 are introduced into the reaction system so as to allow the magnetic particle, the magnetic complex or the agglutination complex to be attached onto the surface of the cover 106. Subsequently, when the turbidity of the reaction system is substantially eliminated, the permanent magnet 105 and the cover 106 are drawn up from the cell 102. Thus, the magnetic particle, the magnetic complex or the agglutination complex can be collected and removed from the reaction system. The magnetic particle, the magnetic complex or the agglutination complex attached onto the cover 106 can be mechanically removed from the cover 106. For example, after removing the cover 106 from the permanent magnet 105, the collected magnetic particle attached onto the cover 106 may be removed by washing, or the cover 106 may be disposable. Alternatively, when an electromagnet is used instead of the permanent magnet 105, the magnetic particles may be collected and removed by turning off the magnetic field generated by the electromagnet.

Figure 10:
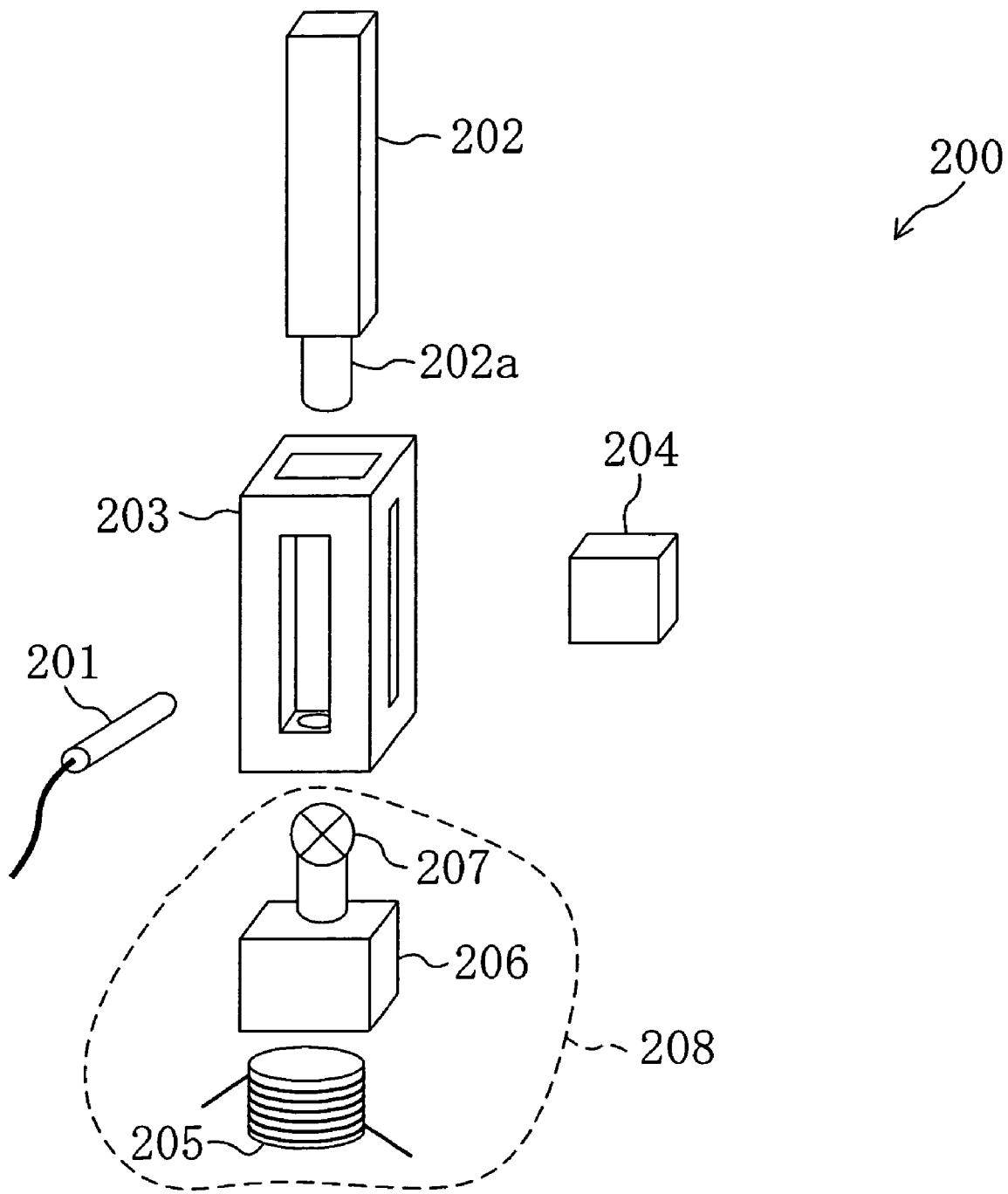
FIG. 10 is a schematic diagram of a measuring apparatus according to another embodiment of the invention.

Next, a measuring apparatus 200 will be described with reference to FIG. 10. FIG. 10 is a schematic diagram of the measuring apparatus 200 of this embodiment.

The measuring apparatus 200 of this embodiment includes, as shown in FIG. 10, a light source 201, a cell (reaction vessel) 202 having an outlet 202a, a cell holder 203 for holding the cell 202, a photodetector 204 for detecting light received from the cell 202 and a removing section 208.

The light source 201 is disposed so that emitted light can proceed to the cell 202.

The photodetector 204 detects scattered light or transmitted light received from a reaction system constructed within the cell 202.

The removing section 208 is used for collecting and removing, by utilizing magnetic force, a magnetic particle, a magnetic complex or an agglutination complex from the reaction system in each of Embodiments 1 through 4. In the measuring apparatus 200, the removing section 208 includes a electromagnet 205, a vessel 206 for storing a substance discharged through the outlet 202a of the cell 202 and an on-off valve 207 to be connected to the outlet 202a of the cell 202.

Figure 11:
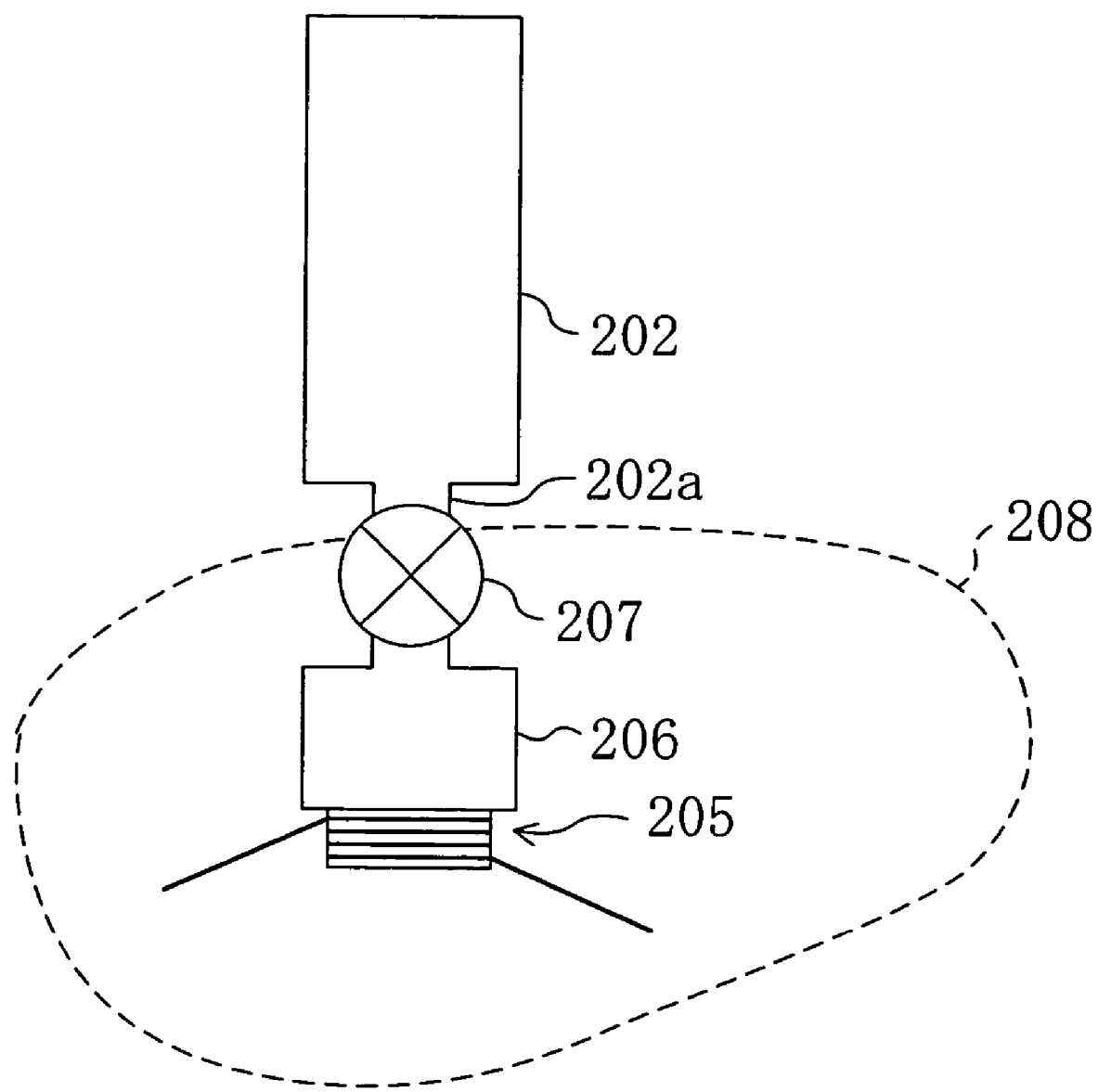
FIG. 11 is a diagram for showing the arrangement relationship in a part of the measuring apparatus of FIG. 10.

Now, the operation of the removing section 208 will be described with reference to FIG. 11. FIG. 11 is a diagram for showing the arrangement relationship between the cell 202 and the removing section 208 in the measuring apparatus 200 of this embodiment.

The valve 207 is connected to the outlet 202a of the cell 202 as shown in FIG. 11. When electric power is supplied to the electromagnet 205 under this condition, a magnetic particle, a magnetic complex or an agglutination complex included in the reaction system within the cell 202 is moved through the outlet 202a and the valve 207 to the vessel 206. Subsequently, when the turbidity of the reaction system is substantially eliminated, the valve 207 is closed and the power supply to the electromagnet 205 is stopped. Thus, the magnetic particle, the magnetic complex or the agglutination complex can be collected and removed from the reaction system. The magnetic particle, the magnetic complex or the agglutination complex stored in the vessel 206 may be removed by washing, or the vessel 206 may be disposable.

In the measuring apparatus 200, the vessel 206 may be replaced with a discharge pipe connected to the cell 202.

Figure 12:
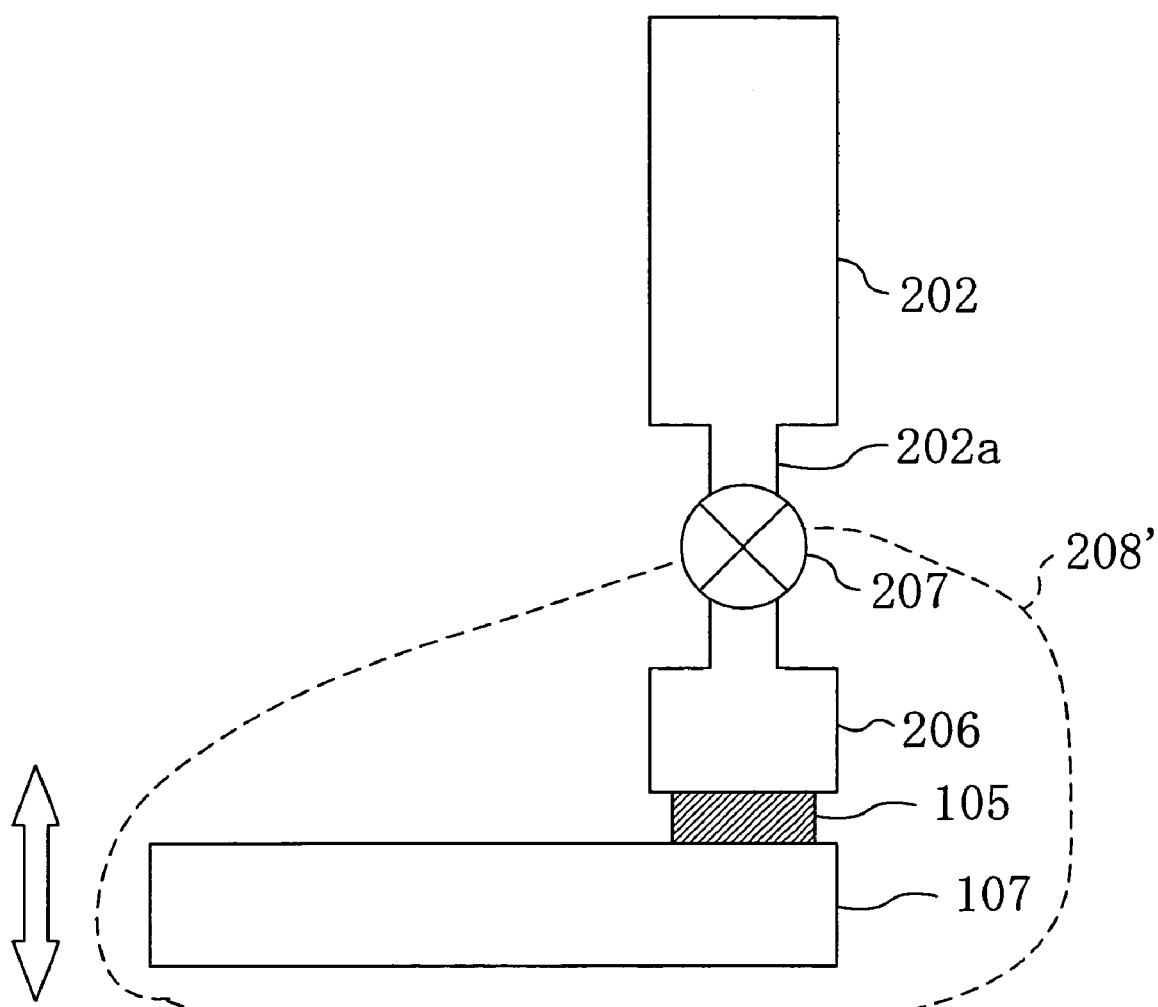
FIG. 12 is a diagram for showing another arrangement relationship in a part of the measuring apparatus of FIG. 10.

Also, in the measuring apparatus 200, the removing section 208 may be replaced with a removing section 208' shown in FIG. 12. As shown in FIG. 12, the removing section 208' includes a permanent magnet 105, an arm 107 for holding the permanent magnet 105, a vessel 206 for storing a substance discharged through the outlet 202a of the cell 202, and an on-off valve 207 connected to the outlet 202a of the cell 202.

The arm 107 can elevate and lower the permanent magnet 105 as shown in FIG. 12. Accordingly, with the permanent magnet 105 placed close to the vessel 206, a magnetic particle, a magnetic complex or an agglutination complex included in the reaction system is discharged to the vessel 206. Subsequently, when the turbidity of the reaction system is substantially eliminated, the valve 207 is closed and the permanent magnet 105 is moved away from the vessel 206. Thus, the magnetic particle, the magnetic complex or the agglutination complex can be collected and removed from the reaction system. The magnetic particle, the magnetic complex or the agglutination complex stored in the vessel 206 may be removed by washing or the vessel 206 may be disposable.

In the case where the removing section 108 or 208' including the permanent magnet 105 is used, the removing section 108 or 208' is preferably operated with the permanent magnet 105 placed away from the cell 202 during the measurement of the optical characteristic of the reaction system, so that the magnetic particle, the magnetic complex or the agglutination complex contained in the cell 202 can be collected and removed after completing the measurement.

In the case where the removing section 208 including the electromagnet 205 is used, the electromagnet 205 may be placed close to the cell 202. This is because the electromagnet 205 minimally generates magnetic force without electric power supply. Accordingly, the removing section 208 is preferably operated so as not to generate the magnetic force by not supplying electric power during the measurement of the optical characteristic of the reaction system and to generate the magnetic force by supplying the electric power for collecting and removing the magnetic particle, the magnetic complex or the agglutination complex from the cell 202 after completing the measurement. This is because, in either case, the influence of the magnetic force on an antigen-antibody reaction can be minimized in the measurement of the optical characteristic of the reaction system.

At this point, the vessel 206 is preferably filled with a buffer equivalent to the reaction system. Thus, change in the volume of the reaction system within the cell 202 can be reduced. Also, since the change in the volume of the reaction system within the cell 202 can be thus reduced, in the measurement of the optical characteristic of the reaction system, the volume of an added reagent alone should be considered in the measurement. Accordingly, the concentration of a subject substance can be easily estimated on the basis of the measure value of the optical characteristic.

EXAMPLE

An example of the invention will now be described in detail. It is noted that the present invention is not limited to the following example.

In this example, a reagent kit according to Embodiment 2 will be described assuming that the first subject substance is human hemoglobin, that the second subject substance is human albumin, that the first specific coupling substance is an anti-human hemoglobin antibody, that the second specific coupling substance is an anti-human albumin antibody, and that the second specific coupling substance is not immobilized on a nonmagnetic particle.

For preparing buffers and the like in this example, purified water filtered with Milli-Q SP TOC (manufactured by Millipore) was used. Also, reagents such as a salt and a buffer not particularly described were all available from Wako Pure Chemical Industries, Ltd., an extra pure reagent was used as polyethylene glycol 6,000 and reagent chemicals were used as other reagents.

The anti-human hemoglobin antibody used as the first specific coupling substance and the anti-human albumin antibody used as the second specific coupling substance were prepared as follows:

First, the anti-human albumin antibody was prepared by purifying, through protein A column chromatography, IgG fractions from an antiserum collected from a rabbit immunized to human albumin (manufactured by Wako Pure Chemical Industries, Ltd.). The protein A immobilization gel filled in the column was one manufactured by Amersham Pharmacia Biotech. An equilibrium buffer used in the purification had a composition of 1.5 M of glycine and 3.0 M of NaCl with pH 8.9. An elution buffer had a composition of 0.1 M of citric acid with pH 4.0.

The purification was carried out as follows: After the equilibrium buffer in the volume five times of the volume of the gel filled in the column was allowed to pass through the column to equilibrate the column, the antiserum including the antibody in the quantity corresponding to 10 through 20% of the total couple volume of the column was diluted twofold with the equilibrium buffer, and the diluted antiserum was allowed to pass through the column so that the antibody included in the antiserum could be coupled with protein A. Subsequently, the equilibrium buffer was allowed to pass through the column until a serum component not adsorbed to protein A did not come out of the column, and the column was washed. Thereafter, the elution buffer was allowed to pass through the column so as to elute the antibody coupled with protein A. The thus eluted fractions of the antibody were placed in a dialysis tube with molecular cutoff of 10,000 and dialyzed several times with a buffer in substantially a 100-fold volume with a composition of 0.05 M of 3-(N-morpholino)propanesulfonic acid (manufactured by Dojin; hereinafter referred to as MOPS), 0.15 M of NaCl and 0.04 wt % of $NaN_3$ with pH 7.4, so as to substitute the buffer component. Subsequently, the concentration of the antibody was estimated through the absorptiometric analysis at 280 nm, so as to be set to 3.0 mg/ml by adjusting with the buffer the same as that used in the dialysis. The resultant solution was used as an anti-human albumin antibody solution. The concentration of the antibody is not limited to that herein described. The thus prepared antibody solution can be stored at room temperature, and is stored preferably at a lower temperature and more preferably at 4° C. for avoiding modification of the antibody.

The anti-human hemoglobin antibody was prepared by purifying, through protein G column chromatography, IgG fractions from an antiserum collected from a goat immunized to human hemoglobin (manufactured by SIGMA; Cat. No. H-7379) and immobilizing the fractions on magnetic particles. The protein G immobilization gel filled in the column used for purifying the IgG fractions was one manufactured by Amersham Pharmacia Biotech. An equilibrium buffer used in the purification had a composition of 0.02 M of $Na_2HPO_4$—$NaH_2PO_4$ with pH 7.0. An elution buffer had a composition of 0.1 M of glycine with pH 2.7. A buffer used in the dialysis had a composition of 0.05 M of MOPS, 0.15 M of NaCl and 0.04 wt % of $NaN_3$ with pH 7.4. The procedures in the purification by the column chromatography and in the dialysis for substituting the buffer were the same as those employed for preparing the anti-human albumin antibody.

Subsequently, the concentration of the antibody was estimated through the absorptiometric analysis at 280 nm, so as to be set to 3.0 mg/ml by adjusting with the buffer the same as that used in the dialysis. The resultant solution was used as an anti-human hemoglobin antibody solution used for immobilizing the anti-human hemoglobin antibody on the magnetic particles.

The magnetic particles can be prepared or are commercially available. In this example, iron-containing polystyrene latex particles with a diameter of 1 through 2 μm, specifically, Polystyrene Superparamagnetic Microspheres (trade name), 1–2μ (manufactured by Polysciences; Cat. No. 18190) were used. The antibody was immobilized on the magnetic particles as follows:

First, 0.5 ml of 2.5 wt % magnetic particles was placed in a micro tube, to which 0.5 ml of a buffer with a composition of 0.05 M of MOPS and 0.04 wt % of $NaN_3$ with pH 7.4 was added so as to suspend the magnetic particles. The resultant was centrifuged with a centrifuge (manufactured by TOMY SEIKO Co. Ltd.; Model No. MRX-150) at 12,000 rpm for 30 minutes. Thus, the magnetic particles were precipitated and the supernatant was removed.

Subsequently, 1 ml of a buffer with a composition of 0.05 M of MOPS and 0.04 wt % of $NaN_3$ with pH 7.4 was added to the resultant so as to suspend the magnetic particles. Then, the suspension was centrifuged at 12,000 rpm for 30 minutes, so as to precipitate the magnetic particles, and the supernatant was removed. Such suspension and precipitation through centrifugation of the magnetic particles were repeated again.

Furthermore, 0.9 ml of a buffer with a composition of 0.05 M of MOPS and 0.04 wt % of $NaN_3$ with pH 7.4 was added to the resultant, so as to suspend the magnetic particles. Then, 0.1 ml of the anti-human hemoglobin antibody solution prepared in the aforementioned manner was added to the suspension. The resultant solution was stirred at room temperature overnight with a rotator (manufactured by TAITEC; Model No. RT-50). After the stirring, the resultant was centrifuged at 12,000 rpm for 30 minutes, so as to precipitate the magnetic particles again, and the supernatant was removed. To the resultant, a buffer with a composition of 0.05 M of MSP, 1 wt % of casein sodium and 0.04 wt % of $NaN_3$ with pH 7.4 was added so as to suspend the magnetic particles, and the suspension was stirred with a rotator for 30 minutes. After the stirring, the resultant was centrifuged at 12,000 rpm for 30 minutes, so as to precipitate the magnetic particles. Such suspension and precipitation through centrifugation of the magnetic particles were repeated three times in total. Thus, the surfaces of the magnetic particles on which the antibody was not immobilized were blocked.

Furthermore, a buffer with a composition of 0.05 M of MOPS, 0.15 M of NaCl, 0.04 wt % of $NaN_3$ and 5 vol % of glycerol with pH 7.4 was added to the resultant, so as to suspend the magnetic particles. It is noted that the concentrations of the antibody and the magnetic particles employed for the immobilization are not limited to those described above. The thus obtained antibody solution can be stored at room temperature, and is stored preferably at a lower temperature and more preferably at 4° C. for avoiding modification of the antibody.

Also, a buffer with a composition of 0.05 M of MOPS and 0.04 wt % of $NaN_3$ with pH 7.4 was prepared as a first buffer to be added to the reaction system for measuring human hemoglobin, and a buffer with a composition of 0.05 M of MOPS, 8.6 wt % of polyethylene glycol 6,000 and 0.04 wt % of $NaN_3$ with pH 7.4 was prepared as a second buffer to be added to the reaction system for measuring human albumin. These buffers were stored at room temperature.

The magnetic particles on which the anti-human hemoglobin antibody (the first specific coupling substance) is immobilized, the anti-human albumin antibody (the second specific coupling substance) and the buffers prepared in the aforementioned manner are combined to give the reagent kit to be used in the specific coupling reaction measuring method.

The reagent kit is used as follows: First, a sample including two subject substances (namely, human hemoglobin and human albumin), the magnetic particle on which the anti-human hemoglobin antibody (the first specific coupling substance) was immobilized and the first buffer were mixed to construct a reaction system. Next, an optical characteristic of the reaction system was measured. After the measurement, an agglutination complex including the human hemoglobin (the first subject substance), the anti-human hemoglobin antibody (the first specific coupling substance) and the magnetic particle, and other excessive magnetic particles not forming any agglutination complex were collected by utilizing magnetic force, so as to eliminate the turbidity of the reaction system.

Subsequently, the anti-human albumin antibody (the second specific coupling substance) and the second buffer were mixed with the reaction system. Thereafter, an optical characteristic of the resultant reaction system was measured. In this manner, the concentrations of the subject substances in the sample could be obtained.

Although not described in this example, the anti-human albumin antibody (the second specific coupling substance) may be immobilized on a nonmagnetic particle of latex or gold colloid. For immobilizing the antibody on, for example, latex particles, the aforementioned immobilization method used for the magnetic particles can be directly employed.

Although the surfaces of the particles on which the antibody is not immobilized are blocked with casein sodium in this example, casein sodium may be replaced with gelatin, skimmed milk or the like. In this case, the concentration of gelatin or the like can be the same as that of casein sodium.

Furthermore, the buffers were prepared with respect to the respective subject substances for constructing the reaction systems in this example, but one kind of buffer including a water-soluble polymer such as polyethylene glycol can be used for constructing the respective reaction systems.

Moreover, the buffer components and the pH of the antibody solutions are not limited to those described above as far as they do not harmfully affect the specific coupling reaction through the coupling between the antigen and the antibody.

Furthermore, in order to take out hemoglobin from erythrocyte, a hemolyzing agent such as potassium chloride may be added to the reaction system or a solution including a hemolyzing agent may be included in the reagent kit.

As described so far, according to the specific coupling reaction measuring method and the reagent kit of the present invention, two or more kinds of subject substances can be measured within merely one reaction vessel.

Accordingly, the present invention provides the specific coupling reaction measuring method in which two or more kinds of subject substances can be measured within one reaction vessel and the quantity of a sample necessary for the measurement can be reduced, and the reagent kit and the measuring apparatus used in the specific coupling reaction measuring method.

The specific coupling reaction measuring method, and the reagent kit and the specific coupling reaction measuring apparatus for use in the method according to the present invention are useful for diagnosis of various diseases and examination of the progressing condition of a disease. When the present invention is applied to measure, for example, human hemoglobin and human albumin in one sample, it is useful for diagnosis of kidney diseases.

What is claimed is:

1. A specific coupling reaction measuring method for measuring a plurality of subject substances in a sample, comprising the steps of:
   (a) constructing a reaction system including said sample and magnetic particles on which a specific coupling substance for specifically coupling with a first subject substance is immobilized;
   (b) measuring an optical characteristic of said reaction system;
   (c) after the step (b), removing, from said reaction system, an agglutination complex including said subject substance, said specific coupling substance and said magnetic particles by utilizing magnetic force;
   (d) after the step (c), adding to said reaction system, which includes said sample, another specific coupling substance for specifically coupling with another subject substance;
   wherein said another specific coupling substance includes an antigen or antibody for specifically coupling with said another subject substance; and
   (e) measuring the optical characteristic of said reaction system after the step (d).

2. The specific coupling reaction measuring method of claim 1, wherein said optical characteristic is an intensity of scattered light or a quantity of transmitted light.

3. The specific coupling reaction measuring method of claim 1, wherein each of said magnetic particles has a diameter of approximately 0.05 through 2 µm.

4. The specific coupling reaction measuring method of claim 1, wherein a portion of said magnetic particles are included in said agglutination complex in an amount necessary to form said agglutination complex with said subject substance and said specific coupling substance, and other magnetic particles that did not form said agglutination complex remain in said reaction system in the step (a), and said other magnetic particles remaining in said reaction system are removed from said reaction system in the step (c).

5. The specific coupling reaction measuring method of claim 1, wherein said reaction system includes 2 through 6 wt % of polyethylene glycol in the step (d).

6. The specific coupling reaction measuring method of claim 1, further comprising a nonmagnetic particle on which said antigen or antibody is immobilized.

7. The specific coupling reaction measuring method of claim 6, wherein said magnetic particle has a diameter of approximately 0.05 through 2 µm and said nonmagnetic particle has a diameter of approximately 0.05 through 2 µm.

8. The specific coupling reaction measuring method of claim 1, wherein a combination of said subject substance and said another subject substance is a combination of human hemoglobin and human albumin.

* * * * *